US006605287B2

(12) United States Patent
Kousoulas et al.

(10) Patent No.: US 6,605,287 B2
(45) Date of Patent: Aug. 12, 2003

(54) **VACCINES FOR *CHLAMYDIA PSITTACI* INFECTIONS**

(75) Inventors: Konstantin G. Kousoulas, Baton Rouge, LA (US); Vladimir N. Chouljenko, Baton Rouge, LA (US); Abolgasem Baghian, Baton Rouge, LA (US); Thomas N. Tully, Jr., St. Francisville, LA (US)

(73) Assignee: Board of Supervisors of Louisiana State University & Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 09/143,127

(22) Filed: Aug. 28, 1998

(65) Prior Publication Data

US 2002/0136742 A1 Sep. 26, 2002

Related U.S. Application Data

(60) Provisional application No. 60/057,147, filed on Aug. 28, 1997.

(51) Int. Cl.[7] .................... A61K 39/118; A61K 39/00; A61K 31/00; C07K 4/04

(52) U.S. Cl. ............................ 424/263.1; 424/185.1; 424/184.1; 514/2; 530/350; 530/389.5; 530/412; 530/825

(58) Field of Search ........................ 424/263.1, 185.1, 424/184.1; 514/2; 530/350, 389.5, 412, 825

(56) References Cited

U.S. PATENT DOCUMENTS 5,725,863 A 3/1998 Daniels et al. ........... 424/263.1

OTHER PUBLICATIONS

Report and Recommendations of the Panel to Assess the NIH Investment in Research on Gene Therapy. Report of the Meeting held in Dec. 7, 1995.*

Verma et al: Gene therapy–promises, problems and prospects: Nature 389; 239–242, 1997.*

Storz, J., (1988), "Overview of Animal Diseases Induced by Chlamydial Infections", *Microbiology of Chlamydia. CRC Press, Inc.*, p. 167–192, Boca Raton, FL.

Baghian, A. and Schnorr, K.,(1992), "Detection And Antigenicity Of Chlamydial Proteins Which Bind Eukaryotic Cell Membrane Proteins", *Am. J. Vet. Res.* vol. 53, pp. 980–986.

Su, H. and Caldwell, H.D.,(1991), "In Vitro Neutralization of *Chlamydia trachomatis* by Monovalent Fab Antibody Specific To The Major Outer Membrane Protein", *Infect. Immun.* 59:2843–2845.

Baehr, et al.,(1988), "Mapping Antigenic Domains Expressed by *Chlamydia Trachomatis* Major Outer Membrane Protein Genes", *Proc. Natl. Acad. Sci.* (USA) 85:4000–4004.

Pickett, M.A., Everson, J.S. and Clarke, I. N.,(1998) "*Chlamydia psittaci* Ewe Abortion Agent: Complete Nucleotide Sequence Of The Major Outer Membrane Protein Gene", *FEMS Microbiology Letters* 55: 229–234.

Yuan, Y., Zhang, Y. X., Watkins, N.G. and Caldwell, H.D., (1989), "Nucleotide and Deduced Amino Acid Sequences For the Four Variable Domains of the Major Outer Membrane Proteins of 15 *Chlamydia trachomatis* Serovars", *Infect. Immun.* 57:1040–1049.

Peeling, R., McClean, I.W. and Brunham, R.C.,(1984), "In vitro Neutralization of *Chlamydia trachomatis* with Monoclonal Antibodies to an Epitope on the Major Outer Membrane Protein",. *Infect. Immun.* 46:484–488.

Spears, P. and Storz, J,(1979) "Biotyping of *Chlamydia psittaci* Based On Inclusion Morphology and Response to Diethylaminoethyl–Dextran and Cycloheximide", *Infect. Immun.* 24:224–232.

Su et al.,(1988), 'Differential Effect of Trypsin on Infectivity of *Chlamydia trachomatis*: Loss of Infectivity Requires Cleavage of Major Outer Membrane Protein Variable Domains II and IV. *Infect. Immun. 56:2094–2100.*

Baghian, A., Shaffer, L. and Storz, J., (1990) "Antibody Response to Epitopes of Chlamydial Major Outer Membrane Proteins on Infectious Elementary Bodies and of the Reduced Polyarylamide Gel Electrophoresis–Separated Form", *Infection and Immunity*, 58: 1379–1383.

Chouljenko, V., Bahgian, A., Kousoulas, G., Tully, T.and Storz, J., (1996) "Cloning, DNA Sequencing, and Bacterial Expression of the *Chlamydia psittaci* MOMP Protein for Vaccine Purposes", *Joint Meeting of the South Central Branch of the American Society for Microbiology and Mid-South Biochemists*, Nov. 1, 1996.

(List continued on next page.)

*Primary Examiner*—Lynette R. F. Smith
*Assistant Examiner*—Padma Baskar
(74) *Attorney, Agent, or Firm*—Needle & Rosenberg, P.C.

(57) ABSTRACT

Vaccine compositions protective against *Chlamydia psittaci* infections in animals, including but not limited to humans and avian species, comprising an immunogenic amount of a *C. psittaci* major outer membrane protein (MOMP) polypeptide lacking regions VD1 and VD2 are provided. Nucleic acid vectors for the expression of MOMP polypeptides and MOMP polypeptide fusion proteins are disclosed. Nucleic acid vectors encoding a *C. psittaci* major outer membrane protein (MOMP) polypeptide lacking regions VD1 and VD2 useful for genetic, or "naked nucleic acid" vaccination are disclosed. Methods for preventing a *Chlamydia psittaci* infection in a subject using MOMP polypeptides, MOMP polypeptide-fusion proteins, or nucleic acid expression vectors are also provided.

3 Claims, No Drawings

OTHER PUBLICATIONS

Tully, T.N., Baghian, A., Kousoulas, K. G., Storz, J. and Poston, R.,(1996), "Potential Use of Chlamydial 18 kDa Adhesion Protein and Major Outer Membrane Protein as a Vaccine Against *Chlamydia psittaci* Infections in Companion Birds", *Association of Avian Veterinarians Proceedings*, p. 161–162.

Zhang, Y. X., Morrison, S. G., Caldwell, H. D. and Baehr, W., (1989) "Cloning and Sequence Analysis of the Major Outer Membrane Protein Genes of Two *Chlamydia psittaci* Strains", *Infect. Immun.* 57:1621–1625.

Kaltenboeck, B., Kousoulas, K. G. and Storz, J.,(1993) "Structures of and Allelic Diversity and Relationships Among the Major Outer Membrane Protein (ompA) Genes of the Four Chlamydial Species", *Bacteriology*, 175: 487–502.

Tully, T. N., Baghian, A., Kousoulas, K. G., Chouljenko, V., Storz, J. and Ritchie, B., (1997) Preliminary Vaccine Trials Of A Genetically Engineered MOMP *Chlamydia psittaci* Vaccine In Cockatiels (*Nymphicus hollandicus*), *4th Conference of the European Committee of the Association of Avian Veterinarians, London, England May 19–24*.

Tan, T.W., Herring, A.J., Anderson, I.E. and Jones, G.E., (1990) "Protection of Sheep Against *Chlamydia psittaci* Infection With a Subcellular Vaccine Containing the Major Outer Membrane Protein", *Infect. Immun.*, 58: 3101–3108.

Dascher, C., Roll, D. and Bavoil, P. M.,(1993) "Expression and Translocation of the Chlamydial Major Outer Membrane Protein In *Escherichia coli*", Microbial Pathogens, 15:455–467.

Kaltenboeck, B., Heard, D., DeGraves, F and Schmeer, N.,(Sep. 1997) "Use of Synthetic Antigens Improves Detection by Enzyme–Linked Immunosorbent Assay of Antibodies Against Abortigenic *Chlamydia psittaci* in Ruminants", J. Clin. Microbio., 15:2293–2298.

Rank, R. G., Batteiger, B. E. and Soderberg, L.S.F.,(1990) "Immunization Against Chlamydial Genital Infection in Guinea Pigs With UV–Inactivated and Viable Chlamydiae Administered by Different Routes", *Infect. Immun.*, 58: 2599–2605.

Everett, K.D.E., Andersen, A.A., Plaunt, M., and Hatch, T. P.,(1991) "Cloning and Sequence Analysis of the Major Outer Membrane Protein Gene of *Chlamydia psittaci* 6BC", *Infect. Immun.* 59: 2853–2855.

Sandbulte, J., TerWee, J., Wigington, K. and Sabara, M.,(1996) "Evaluation of *Chlamydia psittaci* Subfraction and Subunit Preparations for Their Protective Capacities", *Veterinary Microbiology*, 48: 269–282.

Batteiger, B. E., Rank, R. G and Soderberg,L.S.F., (1990)"Immunization of Guinea Pigs With Isolated Chlamydial Outer Membrane Proteins" *Proceedings of the Seventh International Symposium on Human Chlamydial Infections*, Bowie, W.R., et al. eds., *Cambridge University Press* (*Harrison Hot Springs, B.C.*), p. 265–268.

Knight, S.C., Iqball, S., Woods, C., Stagg, A., Ward, M.E. and Tuffrey, M.,(1995) "A Peptide Of *Chlamydia trachomatis* Shown To Be A Primary T–Cell Epitope In Vitro Induces Cell–Mediated Immunity In Vivo", *Immunology*, 85:8–15.

Allen, J.E., Locksley, R.M. and Stephens, R. S.,(1991) "A Single Peptide From The Major Outer Membrane Protein Of *Chlamydia trachomatis* Elicits T Cell Help For The Production Of Antibodies To Protective Determinants", *Immunology*, 147:674–679.

Stagg, A. J., Elsley, W. A.J., Pickett, M.A., Ward, M.E. and Knight, S.C.,(1993) "Primary Human T–Cell Responses To The Major Outer Membrane Protein Of *Chlamydia trachomatis*", Immunology, 79:1–9.

Wei, M.Q., Norman, J., McCracken, A., Serafin, I., Rush, C., Epping, R., Hafner, L. and Timms, P.,(1993) "PCR Cloning and Expression of a Candidate Vaccine Antigen From the MOMP of the Guinea Pig Inclusion Conjunctivitis Strain of *Chlamydia psittaci", Vaccines 1993, Cold Spring Harbor Laboratory Press*, p. 405–408.

Bavoil, P.M., Loeffelholz, L. M., Batteiger, B. E. and Rank, R. G.,(1990) "Analysis of the Guinea Pig Humoral Immune Response to Variable Domains of the Major Outer Membrane Protein of *Chlamydia psittaci", Proceedings of the Seventh International Symposium on Human Chlamydial Infections*, Bowie, W.R., et al. , eds., *Cambridge University Press* (*Harrison Hot Springs, B.C.*), p. 257–260.

Pal et al. Immunization with an Acellular Vaccine Consisting of the Outer Membrane Complex of *Chlamydia trachomatis* Induces Protein against a Genital Challenge. *Infection and Immunity* 65(8): 3361–3369, Aug. 1997.

Peterson et al. Characterization of the Murine Antibody Response to Peptides Representing the Variable Domains of the Major Outer Membraine Protein of *Chlamydia pneumoniae. Infection and Immunity* 64(8): 3354–3359, Aug. 1996.

* cited by examiner

SEQUENCE LISTING

```
<160> NUMBER OF SEQ ID NOS: 18

<210> SEQ ID NO 1
<211> LENGTH: 222
<212> TYPE: PRT
<213> ORGANISM: Chlamydia psittaci (cockatiel)

<400> SEQUENCE: 1

Gly Ser Ile Thr Gln Gly Val Met Glu Phe Tyr Thr Asp Thr Ser Phe
 1               5                   10                  15

Ser Trp Ser Val Gly Ala Arg Gly Ala Leu Trp Glu Cys Gly Cys Ala
            20                  25                  30

Thr Leu Gly Ala Glu Phe Gln Tyr Ala Gln Ser Asn Pro Lys Ile Glu
        35                  40                  45

Met Leu Asn Val Thr Ser Ser Pro Ala Gln Phe Val Ile His Lys Pro
    50                  55                  60
```

-continued

```
Arg Gly Tyr Lys Gly Ala Ser Ser Asn Phe Pro Leu Pro Ile Thr Ala
65                  70                  75                  80

Gly Thr Thr Glu Ala Thr Asp Thr Lys Ser Ala Thr Ile Lys Tyr His
                85                  90                  95

Glu Trp Gln Val Gly Leu Ala Leu Ser Tyr Arg Leu Asn Met Leu Val
            100                 105                 110

Pro Tyr Ile Gly Val Asn Trp Ser Arg Ala Thr Phe Asp Ala Asp Thr
        115                 120                 125

Ile Arg Ile Ala Gln Pro Lys Leu Lys Ser Glu Ile Leu Asn Ile Thr
    130                 135                 140

Thr Trp Asn Pro Ser Leu Ile Gly Ser Thr Thr Ala Leu Pro Asn Asn
145                 150                 155                 160

Ser Gly Lys Asp Val Leu Ser Asp Val Leu Gln Ile Ala Ser Ile Gln
                165                 170                 175

Ile Asn Lys Met Lys Ser Arg Lys Ala Cys Gly Val Ala Val Gly Ala
            180                 185                 190

Thr Leu Ile Asp Ala Asp Lys Trp Ser Ile Thr Gly Glu Ala Arg Leu
        195                 200                 205

Ile Asn Glu Arg Ala Ala His Met Asn Ala Gln Phe Arg Phe
    210                 215                 220


<210> SEQ ID NO 2
<211> LENGTH: 228
<212> TYPE: PRT
<213> ORGANISM: Chlamydia psittaci  B577

<400> SEQUENCE: 2

Gly Ser Ala Met Ala Ala Asp Gln Leu Pro Asn Val Gly Ile Thr Gln
 1               5                  10                  15

Gly Ile Val Glu Phe Tyr Thr Asp Thr Thr Phe Ser Trp Ser Val Gly
            20                  25                  30

Ala Arg Gly Ala Leu Trp Glu Cys Gly Cys Ala Thr Leu Gly Ala Glu
        35                  40                  45

Phe Gln Tyr Ala Gln Ser Asn Pro Lys Ile Glu Met Leu Asn Val Val
    50                  55                  60

Ser Ser Pro Ala Gln Phe Val Val His Lys Pro Arg Gly Tyr Lys Gly
65                  70                  75                  80

Thr Ala Phe Pro Leu Pro Leu Thr Ala Gly Thr Asp Gln Ala Thr Asp
                85                  90                  95

Thr Lys Ser Ala Thr Ile Lys Tyr His Glu Trp Gln Val Gly Leu Ala
            100                 105                 110

Leu Ser Tyr Arg Leu Asn Met Leu Val Pro Tyr Ile Ser Val Asn Trp
        115                 120                 125

Ser Arg Ala Thr Phe Asp Ala Asp Ala Ile Arg Ile Ala Gln Pro Lys
    130                 135                 140

Leu Ala Ala Ala Val Leu Asn Leu Thr Thr Trp Asn Pro Thr Leu Leu
145                 150                 155                 160

Gly Glu Ala Thr Ala Leu Asp Thr Ser Asn Lys Phe Ala Asp Phe Leu
                165                 170                 175

Gln Ile Ala Ser Ile Gln Ile Asn Lys Met Lys Ser Arg Lys Ala Cys
            180                 185                 190

Gly Val Ala Val Gly Ala Thr Leu Ile Asp Ala Asp Lys Trp Ser Ile
        195                 200                 205

Thr Gly Glu Ala Arg Leu Ile Asn Glu Arg Ala Ala His Met Asn Ala
    210                 215                 220
```

-continued

```
Gln Phe Arg Phe
225


<210> SEQ ID NO 3
<211> LENGTH: 726
<212> TYPE: DNA
<213> ORGANISM: Chlamydia psittaci (cockatiel)
<220> FEATURE:
<221> NAME/KEY: CDS
<222> LOCATION: (1)...(666)

<400> SEQUENCE: 3

gga tcc att acc caa ggt gtt atg gaa ttt tat aca gac aca tca ttt       48
Gly Ser Ile Thr Gln Gly Val Met Glu Phe Tyr Thr Asp Thr Ser Phe
 1               5                  10                  15

tct tgg agc gta ggt gca cgt gga gct tta tgg gaa tgt ggt tgt gca       96
Ser Trp Ser Val Gly Ala Arg Gly Ala Leu Trp Glu Cys Gly Cys Ala
            20                  25                  30

act tta gga gct gag ttc caa tac gct caa tct aat cct aag att gaa      144
Thr Leu Gly Ala Glu Phe Gln Tyr Ala Gln Ser Asn Pro Lys Ile Glu
        35                  40                  45

atg ctc aac gtc act tca agc cca gca caa ttt gtg att cac aaa cca      192
Met Leu Asn Val Thr Ser Ser Pro Ala Gln Phe Val Ile His Lys Pro
    50                  55                  60

aga ggc tat aaa gga gct agc tcg aat ttt cct tta cct ata acg gct      240
Arg Gly Tyr Lys Gly Ala Ser Ser Asn Phe Pro Leu Pro Ile Thr Ala
 65                  70                  75                  80

gga aca aca gaa gct aca gac acc aaa tca gct aca att aaa tac cat      288
Gly Thr Thr Glu Ala Thr Asp Thr Lys Ser Ala Thr Ile Lys Tyr His
                85                  90                  95

gaa tgg caa gta ggc ctc gcc ctg tct tac aga ttg aat atg ctt gtt      336
Glu Trp Gln Val Gly Leu Ala Leu Ser Tyr Arg Leu Asn Met Leu Val
            100                 105                 110

cca tat att ggc gta aac tgg tca aga gca act ttt gat gct gat act      384
Pro Tyr Ile Gly Val Asn Trp Ser Arg Ala Thr Phe Asp Ala Asp Thr
        115                 120                 125

atc cgc att gct caa cct aaa tta aaa tcg gag att ctt aac att act      432
Ile Arg Ile Ala Gln Pro Lys Leu Lys Ser Glu Ile Leu Asn Ile Thr
    130                 135                 140

aca tgg aac cca agc ctt ata gga tca acc act gct ttg ccc aat aat      480
Thr Trp Asn Pro Ser Leu Ile Gly Ser Thr Thr Ala Leu Pro Asn Asn
145                 150                 155                 160

agt ggt aag gat gtt cta tct gat gtc ttg caa att gct tcg att cag      528
Ser Gly Lys Asp Val Leu Ser Asp Val Leu Gln Ile Ala Ser Ile Gln
                165                 170                 175

atc aac aaa atg aag tct aga aaa gct tgt ggt gta gct gtt ggt gca      576
Ile Asn Lys Met Lys Ser Arg Lys Ala Cys Gly Val Ala Val Gly Ala
            180                 185                 190

acg tta atc gac gct gac aaa tgg tca atc act ggt gaa gca cgc tta      624
Thr Leu Ile Asp Ala Asp Lys Trp Ser Ile Thr Gly Glu Ala Arg Leu
        195                 200                 205

atc aat gaa aga gct gct cac atg aat gct caa ttc aga ttc              666
Ile Asn Glu Arg Ala Ala His Met Asn Ala Gln Phe Arg Phe
    210                 215                 220

taaggattta gtttatacta tcctaacttt ttgtcccgct atcagaacct gggagtctcc    726


<210> SEQ ID NO 4
<211> LENGTH: 726
<212> TYPE: DNA
<213> ORGANISM: Chlamydia psittaci (cockatiel)
<220> FEATURE:
```

-continued

```
<221> NAME/KEY: CDS
<222> LOCATION: (1)...(666)

<400> SEQUENCE: 4

gga tcc att acc caa ggt gtt atg gaa ttt tat aca gac aca tca ttt       48
Gly Ser Ile Thr Gln Gly Val Met Glu Phe Tyr Thr Asp Thr Ser Phe
 1               5                  10                  15

tct tgg agc gta ggt gca cgt gga gct tta tgg gaa tgt ggt tgt gca       96
Ser Trp Ser Val Gly Ala Arg Gly Ala Leu Trp Glu Cys Gly Cys Ala
            20                  25                  30

act tta gga gct gag ttc caa tac gct caa tct aat cct aag att gaa      144
Thr Leu Gly Ala Glu Phe Gln Tyr Ala Gln Ser Asn Pro Lys Ile Glu
        35                  40                  45

atg ctc aac gtc act tca agc cca gca caa ttt gtg att cac aaa cca      192
Met Leu Asn Val Thr Ser Ser Pro Ala Gln Phe Val Ile His Lys Pro
    50                  55                  60

aga ggc tat aaa gga gct agc tcg aat ttt cct tta cct ata acg gct      240
Arg Gly Tyr Lys Gly Ala Ser Ser Asn Phe Pro Leu Pro Ile Thr Ala
 65                  70                  75                  80

gga aca aca gaa gct aca gac acc aaa tca gct aca att aaa tac cat      288
Gly Thr Thr Glu Ala Thr Asp Thr Lys Ser Ala Thr Ile Lys Tyr His
                85                  90                  95

gaa tgg caa gta ggc ctc gcc ctg tct tac aga ttg aat atg ctt gtt      336
Glu Trp Gln Val Gly Leu Ala Leu Ser Tyr Arg Leu Asn Met Leu Val
            100                 105                 110

cca tat att ggc gta aac tgg tca aga gca act ttt gat gct gat act      384
Pro Tyr Ile Gly Val Asn Trp Ser Arg Ala Thr Phe Asp Ala Asp Thr
        115                 120                 125

atc cgc att gct caa cct aaa tta aaa tcg gag att ctt aac att act      432
Ile Arg Ile Ala Gln Pro Lys Leu Lys Ser Glu Ile Leu Asn Ile Thr
    130                 135                 140

aca tgg aac cca agc ctt ata gga tca acc act gct ttg ccc aat aat      480
Thr Trp Asn Pro Ser Leu Ile Gly Ser Thr Thr Ala Leu Pro Asn Asn
145                 150                 155                 160

agt ggt aag gat gtt cta tct gat gtc ttg caa att gct tcg att cag      528
Ser Gly Lys Asp Val Leu Ser Asp Val Leu Gln Ile Ala Ser Ile Gln
                165                 170                 175

atc aac aaa atg aag tct aga aaa gct tgt ggt gta gct gtt ggt gca      576
Ile Asn Lys Met Lys Ser Arg Lys Ala Cys Gly Val Ala Val Gly Ala
            180                 185                 190

acg tta atc gac gct gac aaa tgg tca atc act ggt gaa gca cgc tta      624
Thr Leu Ile Asp Ala Asp Lys Trp Ser Ile Thr Gly Glu Ala Arg Leu
        195                 200                 205

atc aat gaa aga gct gct cac atg aat gct caa ttc aga ttc              666
Ile Asn Glu Arg Ala Ala His Met Asn Ala Gln Phe Arg Phe
    210                 215                 220

taaggattta gtttatacta tcctaacttt ttgtcccgct atcagaacct gggagtctcc    726


<210> SEQ ID NO 5
<211> LENGTH: 744
<212> TYPE: DNA
<213> ORGANISM: Chlamydia psittaci B577
<220> FEATURE:
<221> NAME/KEY: CDS
<222> LOCATION: (1)...(684)

<400> SEQUENCE: 5

gga tcc gcc atg gca gct gat cag ctt ccc aat gta ggc atc act caa       48
Gly Ser Ala Met Ala Ala Asp Gln Leu Pro Asn Val Gly Ile Thr Gln
 1               5                  10                  15

gga atc gtt gaa ttt tat aca gat aca aca ttc tct tgg agt gta ggt       96
```

-continued

```
Gly Ile Val Glu Phe Tyr Thr Asp Thr Thr Phe Ser Trp Ser Val Gly
             20                  25                  30

gca cgc gga gct tta tgg gag tgt ggt tgt gcg act tta gga gca gag      144
Ala Arg Gly Ala Leu Trp Glu Cys Gly Cys Ala Thr Leu Gly Ala Glu
        35                  40                  45

ttc caa tac gct cag tct aat cct aaa att gaa atg ttg aat gta gtc      192
Phe Gln Tyr Ala Gln Ser Asn Pro Lys Ile Glu Met Leu Asn Val Val
    50                  55                  60

tcc agc cca gca caa ttt gtg gtt cac aag cct aga gga tac aag gga      240
Ser Ser Pro Ala Gln Phe Val Val His Lys Pro Arg Gly Tyr Lys Gly
 65                  70                  75                  80

aca gca ttt cct tta cct cta aca gct ggt act gat cag gca act gac      288
Thr Ala Phe Pro Leu Pro Leu Thr Ala Gly Thr Asp Gln Ala Thr Asp
                 85                  90                  95

act aag tcg gct aca att aaa tac cac gaa tgg caa gtt ggt tta gcg      336
Thr Lys Ser Ala Thr Ile Lys Tyr His Glu Trp Gln Val Gly Leu Ala
            100                 105                 110

ctc tct tat cga ttg aac atg ctt gtt cct tac att agc gta aac tgg      384
Leu Ser Tyr Arg Leu Asn Met Leu Val Pro Tyr Ile Ser Val Asn Trp
        115                 120                 125

tca cga gca act ttt gat gct gac gct atc cgc atc gct caa cct aaa      432
Ser Arg Ala Thr Phe Asp Ala Asp Ala Ile Arg Ile Ala Gln Pro Lys
    130                 135                 140

tta gct gct gct gtg tta aac ttg acc aca tgg aac cca acc ctt tta      480
Leu Ala Ala Ala Val Leu Asn Leu Thr Thr Trp Asn Pro Thr Leu Leu
145                 150                 155                 160

gga gaa gct aca gct tta gat act agc aac aaa ttc gct gac ttc ttg      528
Gly Glu Ala Thr Ala Leu Asp Thr Ser Asn Lys Phe Ala Asp Phe Leu
                165                 170                 175

caa att gct tcg att cag atc aac aaa atg aag tct aga aaa gct tgt      576
Gln Ile Ala Ser Ile Gln Ile Asn Lys Met Lys Ser Arg Lys Ala Cys
            180                 185                 190

ggt gta gct gtt ggt gca acg tta atc gac gct gac aaa tgg tca atc      624
Gly Val Ala Val Gly Ala Thr Leu Ile Asp Ala Asp Lys Trp Ser Ile
        195                 200                 205

act ggt gaa gca cgc tta atc aat gaa aga gcc gct cac atg aat gct      672
Thr Gly Glu Ala Arg Leu Ile Asn Glu Arg Ala Ala His Met Asn Ala
    210                 215                 220

caa ttc aga ttc taaggattta gtttatacta tcctaacttt ttgtcccgct          724
Gln Phe Arg Phe
225

atcagaacct aggaattcgt                                                744


<210> SEQ ID NO 6
<211> LENGTH: 687
<212> TYPE: DNA
<213> ORGANISM: Chlamydia psittaci B577
<220> FEATURE:
<221> NAME/KEY: CDS
<222> LOCATION: (1)...(684)

<400> SEQUENCE: 6

gga tcc gcc atg gca gct gat cag ctt ccc aat gta ggc atc act caa       48
Gly Ser Ala Met Ala Ala Asp Gln Leu Pro Asn Val Gly Ile Thr Gln
 1               5                  10                  15

gga atc gtt gaa ttt tat aca gat aca aca ttc tct tgg agt gta ggt       96
Gly Ile Val Glu Phe Tyr Thr Asp Thr Thr Phe Ser Trp Ser Val Gly
             20                  25                  30

gca cgc gga gct tta tgg gag tgt ggt tgt gcg act tta gga gca gag      144
Ala Arg Gly Ala Leu Trp Glu Cys Gly Cys Ala Thr Leu Gly Ala Glu
        35                  40                  45
```

-continued ttc caa tac gct cag tct aat cct aaa att gaa atg ttg aat gta gtc 192
Phe Gln Tyr Ala Gln Ser Asn Pro Lys Ile Glu Met Leu Asn Val Val
50 55 60 tcc agc cca gca caa ttt gtg gtt cac aag cct aga gga tac aag gga 240
Ser Ser Pro Ala Gln Phe Val Val His Lys Pro Arg Gly Tyr Lys Gly
65 70 75 80 aca gca ttt cct tta cct cta aca gct ggt act gat cag gca act gac 288
Thr Ala Phe Pro Leu Pro Leu Thr Ala Gly Thr Asp Gln Ala Thr Asp
85 90 95 act aag tcg gct aca att aaa tac cac gaa tgg caa gtt ggt tta gcg 336
Thr Lys Ser Ala Thr Ile Lys Tyr His Glu Trp Gln Val Gly Leu Ala
100 105 110 ctc tct tat cga ttg aac atg ctt gtt cct tac att agc gta aac tgg 384
Leu Ser Tyr Arg Leu Asn Met Leu Val Pro Tyr Ile Ser Val Asn Trp
115 120 125 tca cga gca act ttt gat gct gac gct atc cgc atc gct caa cct aaa 432
Ser Arg Ala Thr Phe Asp Ala Asp Ala Ile Arg Ile Ala Gln Pro Lys
130 135 140 tta gct gct gct gtg tta aac ttg acc aca tgg aac cca acc ctt tta 480
Leu Ala Ala Ala Val Leu Asn Leu Thr Thr Trp Asn Pro Thr Leu Leu
145 150 155 160 gga gaa gct aca gct tta gat act agc aac aaa ttc gct gac ttc ttg 528
Gly Glu Ala Thr Ala Leu Asp Thr Ser Asn Lys Phe Ala Asp Phe Leu
165 170 175 caa att gct tcg att cag atc aac aaa atg aag tct aga aaa gct tgt 576
Gln Ile Ala Ser Ile Gln Ile Asn Lys Met Lys Ser Arg Lys Ala Cys
180 185 190 ggt gta gct gtt ggt gca acg tta atc gac gct gac aaa tgg tca atc 624
Gly Val Ala Val Gly Ala Thr Leu Ile Asp Ala Asp Lys Trp Ser Ile
195 200 205 act ggt gaa gca cgc tta atc aat gaa aga gcc gct cac atg aat gct 672
Thr Gly Glu Ala Arg Leu Ile Asn Glu Arg Ala Ala His Met Asn Ala
210 215 220 caa ttc aga ttc taa 687
Gln Phe Arg Phe
225

<210> SEQ ID NO 7
<211> LENGTH: 215
<212> TYPE: PRT
<213> ORGANISM: Chlamydia psittaci (cockatiel)

<400> SEQUENCE: 7

Met Glu Phe Tyr Thr Asp Thr Ser Phe Ser Trp Ser Val Gly Ala Arg
1 5 10 15

Gly Ala Leu Trp Glu Cys Gly Cys Ala Thr Leu Gly Ala Glu Phe Gln
20 25 30

Tyr Ala Gln Ser Asn Pro Lys Ile Glu Met Leu Asn Val Thr Ser Ser
35 40 45

Pro Ala Gln Phe Val Ile His Lys Pro Arg Gly Tyr Lys Gly Ala Ser
50 55 60

Ser Asn Phe Pro Leu Pro Ile Thr Ala Gly Thr Thr Glu Ala Thr Asp
65 70 75 80

Thr Lys Ser Ala Thr Ile Lys Tyr His Glu Trp Gln Val Gly Leu Ala
85 90 95

Leu Ser Tyr Arg Leu Asn Met Leu Val Pro Tyr Ile Gly Val Asn Trp
100 105 110

Ser Arg Ala Thr Phe Asp Ala Asp Thr Ile Arg Ile Ala Gln Pro Lys

-continued 115 120 125

Leu Lys Ser Glu Ile Leu Asn Ile Thr Thr Trp Asn Pro Ser Leu Ile
130 135 140

Gly Ser Thr Thr Ala Leu Pro Asn Asn Ser Gly Lys Asp Val Leu Ser
145 150 155 160

Asp Val Leu Gln Ile Ala Ser Ile Gln Ile Asn Lys Met Lys Ser Arg
165 170 175

Lys Ala Cys Gly Val Ala Val Gly Ala Thr Leu Ile Asp Ala Asp Lys
180 185 190

Trp Ser Ile Thr Gly Glu Ala Arg Leu Ile Asn Glu Arg Ala Ala His
195 200 205

Met Asn Ala Gln Phe Arg Phe
210 215

<210> SEQ ID NO 8
<211> LENGTH: 225
<212> TYPE: PRT
<213> ORGANISM: Chlamydia psittaci B577

<400> SEQUENCE: 8

Met Ala Ala Asp Gln Leu Pro Asn Val Gly Ile Thr Gln Gly Ile Val
1 5 10 15

Glu Phe Tyr Thr Asp Thr Thr Phe Ser Trp Ser Val Gly Ala Arg Gly
20 25 30

Ala Leu Trp Glu Cys Gly Cys Ala Thr Leu Gly Ala Glu Phe Gln Tyr
35 40 45

Ala Gln Ser Asn Pro Lys Ile Glu Met Leu Asn Val Val Ser Ser Pro
50 55 60

Ala Gln Phe Val Val His Lys Pro Arg Gly Tyr Lys Gly Thr Ala Phe
65 70 75 80

Pro Leu Pro Leu Thr Ala Gly Thr Asp Gln Ala Thr Asp Thr Lys Ser
85 90 95

Ala Thr Ile Lys Tyr His Glu Trp Gln Val Gly Leu Ala Leu Ser Tyr
100 105 110

Arg Leu Asn Met Leu Val Pro Tyr Ile Ser Val Asn Trp Ser Arg Ala
115 120 125

Thr Phe Asp Ala Asp Ala Ile Arg Ile Ala Gln Pro Lys Leu Ala Ala
130 135 140

Ala Val Leu Asn Leu Thr Thr Trp Asn Pro Thr Leu Leu Gly Glu Ala
145 150 155 160

Thr Ala Leu Asp Thr Ser Asn Lys Phe Ala Asp Phe Leu Gln Ile Ala
165 170 175

Ser Ile Gln Ile Asn Lys Met Lys Ser Arg Lys Ala Cys Gly Val Ala
180 185 190

Val Gly Ala Thr Leu Ile Asp Ala Asp Lys Trp Ser Ile Thr Gly Glu
195 200 205

Ala Arg Leu Ile Asn Glu Arg Ala Ala His Met Asn Ala Gln Phe Arg
210 215 220

Phe
225

<210> SEQ ID NO 9
<211> LENGTH: 1209
<212> TYPE: DNA
<213> ORGANISM: Chlamydia psittaci Avian Type C
<220> FEATURE:

-continued

<221> NAME/KEY: CDS
<222> LOCATION: (1)...(1206)

<400> SEQUENCE: 9

```
atg aaa aaa ctc ttg aaa tcg gca tta ttg ttt gcc gct acg ggt tcc       48
Met Lys Lys Leu Leu Lys Ser Ala Leu Leu Phe Ala Ala Thr Gly Ser
 1               5                  10                  15

gct ctc tcc tta caa gcc ttg cct gta ggg aac cca gct gaa cca agt       96
Ala Leu Ser Leu Gln Ala Leu Pro Val Gly Asn Pro Ala Glu Pro Ser
            20                  25                  30

tta tta atc gat ggc act atg tgg gaa ggt gct tca gga gat cct tgc      144
Leu Leu Ile Asp Gly Thr Met Trp Glu Gly Ala Ser Gly Asp Pro Cys
        35                  40                  45

gat cct tgc gct act tgg tgt gac gcc att agc atc cgc gca gga tac      192
Asp Pro Cys Ala Thr Trp Cys Asp Ala Ile Ser Ile Arg Ala Gly Tyr
    50                  55                  60

tac gga gat tat gtt ttc gat cgt gta tta aaa gtt gat gtg aat aaa      240
Tyr Gly Asp Tyr Val Phe Asp Arg Val Leu Lys Val Asp Val Asn Lys
 65                  70                  75                  80

act ttt agc ggc atg gct gca act cct acg cag gct aca ggt aac gca      288
Thr Phe Ser Gly Met Ala Ala Thr Pro Thr Gln Ala Thr Gly Asn Ala
                 85                  90                  95

agt aat act aat cag cca gaa gca aat ggc aga ccg aac atc gct tac      336
Ser Asn Thr Asn Gln Pro Glu Ala Asn Gly Arg Pro Asn Ile Ala Tyr
            100                 105                 110

gga agg cat atg gaa gat gca gag tgg ttt tca aat gca gcc ttc cta      384
Gly Arg His Met Glu Asp Ala Glu Trp Phe Ser Asn Ala Ala Phe Leu
        115                 120                 125

gcc tta aac att tgg gat cgc ttc gac att tac tgc acc tta ggg gca      432
Ala Leu Asn Ile Trp Asp Arg Phe Asp Ile Tyr Cys Thr Leu Gly Ala
    130                 135                 140

tcc aat gga tac ttc aaa gca agt tcg gct gca ttc aac ttg gtt ggg      480
Ser Asn Gly Tyr Phe Lys Ala Ser Ser Ala Ala Phe Asn Leu Val Gly
145                 150                 155                 160

tta ata ggg ttt tca gct gca agc tca atc tct acc gat ctt cca acg      528
Leu Ile Gly Phe Ser Ala Ala Ser Ser Ile Ser Thr Asp Leu Pro Thr
                165                 170                 175

caa ctt cct aac gta ggc att acc caa ggt gtt gtg gaa ttt tat aca      576
Gln Leu Pro Asn Val Gly Ile Thr Gln Gly Val Val Glu Phe Tyr Thr
            180                 185                 190

gac aca tca ttt tct tgg agc gta ggt gca cgt gga gct tta tgg gaa      624
Asp Thr Ser Phe Ser Trp Ser Val Gly Ala Arg Gly Ala Leu Trp Glu
        195                 200                 205

tgt ggt tgt gca act tta gga gct gag ttc caa tac gct caa tct aat      672
Cys Gly Cys Ala Thr Leu Gly Ala Glu Phe Gln Tyr Ala Gln Ser Asn
    210                 215                 220

cct aag att gaa atg ctc aac gtc act tca agc cca gca caa ttt gtg      720
Pro Lys Ile Glu Met Leu Asn Val Thr Ser Ser Pro Ala Gln Phe Val
225                 230                 235                 240

att cac aaa cca aga ggc tat aaa gga gct agc tcg aat ttt cct tta      768
Ile His Lys Pro Arg Gly Tyr Lys Gly Ala Ser Ser Asn Phe Pro Leu
                245                 250                 255

cct ata acg gct gga aca aca gaa gct aca gac acc aaa tca gct aca      816
Pro Ile Thr Ala Gly Thr Thr Glu Ala Thr Asp Thr Lys Ser Ala Thr
            260                 265                 270

att aaa tac cat gaa tgg caa gta ggc ctc gcc ctg tct tac aga ttg      864
Ile Lys Tyr His Glu Trp Gln Val Gly Leu Ala Leu Ser Tyr Arg Leu
        275                 280                 285

aat atg ctt gtt cca tat att ggc gta aac tgg tca aga gca act ttt      912
Asn Met Leu Val Pro Tyr Ile Gly Val Asn Trp Ser Arg Ala Thr Phe
```

-continued

```
    290                 295                 300

gat gct gat act atc cgc att gct caa cct aaa tta aaa tcg gag att      960
Asp Ala Asp Thr Ile Arg Ile Ala Gln Pro Lys Leu Lys Ser Glu Ile
305                 310                 315                 320

ctt aac att act aca tgg aac cca agc ctt ata gga tca acc act gct     1008
Leu Asn Ile Thr Thr Trp Asn Pro Ser Leu Ile Gly Ser Thr Thr Ala
                325                 330                 335

ttg ccc aat aat agt ggt aag gat gtt cta tct gat gtc ttg caa att     1056
Leu Pro Asn Asn Ser Gly Lys Asp Val Leu Ser Asp Val Leu Gln Ile
            340                 345                 350

gct tcg att cag atc aac aaa atg aag tct aga aaa gct tgt ggt gta     1104
Ala Ser Ile Gln Ile Asn Lys Met Lys Ser Arg Lys Ala Cys Gly Val
        355                 360                 365

gct gtt ggt gca acg tta atc gac gct gac aaa tgg tca atc act ggt     1152
Ala Val Gly Ala Thr Leu Ile Asp Ala Asp Lys Trp Ser Ile Thr Gly
    370                 375                 380

gaa gca cgc tta atc aat gaa aga gct gct cac atg aat gct caa ttc     1200
Glu Ala Arg Leu Ile Asn Glu Arg Ala Ala His Met Asn Ala Gln Phe
385                 390                 395                 400

aga ttc taa                                                         1209
Arg Phe


<210> SEQ ID NO 10
<211> LENGTH: 402
<212> TYPE: PRT
<213> ORGANISM: Chlamydia psittaci Avian Type C

<400> SEQUENCE: 10

Met Lys Lys Leu Leu Lys Ser Ala Leu Leu Phe Ala Ala Thr Gly Ser
 1               5                  10                  15

Ala Leu Ser Leu Gln Ala Leu Pro Val Gly Asn Pro Ala Glu Pro Ser
            20                  25                  30

Leu Leu Ile Asp Gly Thr Met Trp Glu Gly Ala Ser Gly Asp Pro Cys
        35                  40                  45

Asp Pro Cys Ala Thr Trp Cys Asp Ala Ile Ser Ile Arg Ala Gly Tyr
    50                  55                  60

Tyr Gly Asp Tyr Val Phe Asp Arg Val Leu Lys Val Asp Val Asn Lys
65                  70                  75                  80

Thr Phe Ser Gly Met Ala Ala Thr Pro Thr Gln Ala Thr Gly Asn Ala
                85                  90                  95

Ser Asn Thr Asn Gln Pro Glu Ala Asn Gly Arg Pro Asn Ile Ala Tyr
            100                 105                 110

Gly Arg His Met Glu Asp Ala Glu Trp Phe Ser Asn Ala Ala Phe Leu
        115                 120                 125

Ala Leu Asn Ile Trp Asp Arg Phe Asp Ile Tyr Cys Thr Leu Gly Ala
    130                 135                 140

Ser Asn Gly Tyr Phe Lys Ala Ser Ser Ala Ala Phe Asn Leu Val Gly
145                 150                 155                 160

Leu Ile Gly Phe Ser Ala Ala Ser Ser Ile Ser Thr Asp Leu Pro Thr
                165                 170                 175

Gln Leu Pro Asn Val Gly Ile Thr Gln Gly Val Val Glu Phe Tyr Thr
            180                 185                 190

Asp Thr Ser Phe Ser Trp Ser Val Gly Ala Arg Gly Ala Leu Trp Glu
        195                 200                 205

Cys Gly Cys Ala Thr Leu Gly Ala Glu Phe Gln Tyr Ala Gln Ser Asn
    210                 215                 220
```

-continued

Pro Lys Ile Glu Met Leu Asn Val Thr Ser Ser Pro Ala Gln Phe Val
225 230 235 240

Ile His Lys Pro Arg Gly Tyr Lys Gly Ala Ser Ser Asn Phe Pro Leu
245 250 255

Pro Ile Thr Ala Gly Thr Thr Glu Ala Thr Asp Thr Lys Ser Ala Thr
260 265 270

Ile Lys Tyr His Glu Trp Gln Val Gly Leu Ala Leu Ser Tyr Arg Leu
275 280 285

Asn Met Leu Val Pro Tyr Ile Gly Val Asn Trp Ser Arg Ala Thr Phe
290 295 300

Asp Ala Asp Thr Ile Arg Ile Ala Gln Pro Lys Leu Lys Ser Glu Ile
305 310 315 320

Leu Asn Ile Thr Thr Trp Asn Pro Ser Leu Ile Gly Ser Thr Thr Ala
325 330 335

Leu Pro Asn Asn Ser Gly Lys Asp Val Leu Ser Asp Val Leu Gln Ile
340 345 350

Ala Ser Ile Gln Ile Asn Lys Met Lys Ser Arg Lys Ala Cys Gly Val
355 360 365

Ala Val Gly Ala Thr Leu Ile Asp Ala Asp Lys Trp Ser Ile Thr Gly
370 375 380

Glu Ala Arg Leu Ile Asn Glu Arg Ala Ala His Met Asn Ala Gln Phe
385 390 395 400

Arg Phe

<210> SEQ ID NO 11
<211> LENGTH: 1261
<212> TYPE: DNA
<213> ORGANISM: Chlamydia psittaci B577
<220> FEATURE:
<221> NAME/KEY: CDS
<222> LOCATION: (80)...(1246)

<400> SEQUENCE: 11
acgtggtgcc gccagaagag caaattagaa tagcgagcac aaaaagaaaa gatactaagc 60
ataatcttta gaggtgagt atg aaa aaa ctc ttg aaa tcg gca tta ttg ttt 112
Met Lys Lys Leu Leu Lys Ser Ala Leu Leu Phe
1 5 10 gcc gct acg ggt tcc gct ctc tcc tta caa gcc ttg cct gta ggg aac 160
Ala Ala Thr Gly Ser Ala Leu Ser Leu Gln Ala Leu Pro Val Gly Asn
15 20 25 cca gct gaa cca agt tta tta atc gat ggc act atg tgg gaa ggt gct 208
Pro Ala Glu Pro Ser Leu Leu Ile Asp Gly Thr Met Trp Glu Gly Ala
30 35 40 tca ggt gat cct tgc gat cct tgc tct act tgg tgt gat gct atc agc 256
Ser Gly Asp Pro Cys Asp Pro Cys Ser Thr Trp Cys Asp Ala Ile Ser
45 50 55 atc cgc gca gga tac tac gga gat tat gtt ttc gat cgt gta tta aaa 304
Ile Arg Ala Gly Tyr Tyr Gly Asp Tyr Val Phe Asp Arg Val Leu Lys
60 65 70 75 gtt gat gtg aat aaa act atc acc ggc atg ggt gca gtt cct aca gga 352
Val Asp Val Asn Lys Thr Ile Thr Gly Met Gly Ala Val Pro Thr Gly
80 85 90 acc gca gca gct aat tac aaa act cct acg gat aga ccc aac atc gct 400
Thr Ala Ala Ala Asn Tyr Lys Thr Pro Thr Asp Arg Pro Asn Ile Ala
95 100 105 tac ggc aaa cac tta caa gac gcc gaa tgg ttc acc aat gca gct ttc 448
Tyr Gly Lys His Leu Gln Asp Ala Glu Trp Phe Thr Asn Ala Ala Phe
110 115 120

-continued

```
ctc gca ttg aat atc tgg gat cgc ttt gat att ttc tgc aca tta ggc      496
Leu Ala Leu Asn Ile Trp Asp Arg Phe Asp Ile Phe Cys Thr Leu Gly
    125                 130                 135

gct tct aat ggg tac ttc aaa gct agt tct gcg gca ttc aac ctc gtt      544
Ala Ser Asn Gly Tyr Phe Lys Ala Ser Ser Ala Ala Phe Asn Leu Val
140                 145                 150                 155

ggt ttg att ggt gtt aaa gga tcc tcc ata gca gct gat cag ctt ccc      592
Gly Leu Ile Gly Val Lys Gly Ser Ser Ile Ala Ala Asp Gln Leu Pro
                160                 165                 170

aat gta ggc atc act caa gga atc gtt gaa ttt tat aca gat aca aca      640
Asn Val Gly Ile Thr Gln Gly Ile Val Glu Phe Tyr Thr Asp Thr Thr
            175                 180                 185

ttc tct tgg agt gta ggt gca cgc gga gct tta tgg gag tgt ggt tgt      688
Phe Ser Trp Ser Val Gly Ala Arg Gly Ala Leu Trp Glu Cys Gly Cys
        190                 195                 200

gcg act tta gga gca gag ttc caa tac gct cag tct aat cct aaa att      736
Ala Thr Leu Gly Ala Glu Phe Gln Tyr Ala Gln Ser Asn Pro Lys Ile
    205                 210                 215

gaa atg ttg aat gta gtc tcc agc cca gca caa ttt gtg gtt cac aag      784
Glu Met Leu Asn Val Val Ser Ser Pro Ala Gln Phe Val Val His Lys
220                 225                 230                 235

cct aga gga tac aag gga aca gca ttt cct tta cct cta aca gct ggt      832
Pro Arg Gly Tyr Lys Gly Thr Ala Phe Pro Leu Pro Leu Thr Ala Gly
                240                 245                 250

act gat cag gca act gac act aag tcg gct aca att aaa tac cac gaa      880
Thr Asp Gln Ala Thr Asp Thr Lys Ser Ala Thr Ile Lys Tyr His Glu
            255                 260                 265

tgg caa gtt ggt tta gcg ctc tct tat cga ttg aac atg ctt gtt cct      928
Trp Gln Val Gly Leu Ala Leu Ser Tyr Arg Leu Asn Met Leu Val Pro
        270                 275                 280

tac att agc gta aac tgg tca cga gca act ttt gat gct gac gct atc      976
Tyr Ile Ser Val Asn Trp Ser Arg Ala Thr Phe Asp Ala Asp Ala Ile
    285                 290                 295

cgc atc gct caa cct aaa tta gct gct gct gtg tta aac ttg acc aca     1024
Arg Ile Ala Gln Pro Lys Leu Ala Ala Ala Val Leu Asn Leu Thr Thr
300                 305                 310                 315

tgg aac cca acc ctt tta gga gaa gct aca gct tta gat act agc aac     1072
Trp Asn Pro Thr Leu Leu Gly Glu Ala Thr Ala Leu Asp Thr Ser Asn
                320                 325                 330

aaa ttc gct gac ttc ttg caa att gct tcg att cag atc aac aaa atg     1120
Lys Phe Ala Asp Phe Leu Gln Ile Ala Ser Ile Gln Ile Asn Lys Met
            335                 340                 345

aag tct aga aaa gct tgt ggt gta gct gtt ggt gca acg tta atc gac     1168
Lys Ser Arg Lys Ala Cys Gly Val Ala Val Gly Ala Thr Leu Ile Asp
        350                 355                 360

gct gac aaa tgg tca atc act ggt gaa gca cgc tta atc aat gaa aga     1216
Ala Asp Lys Trp Ser Ile Thr Gly Glu Ala Arg Leu Ile Asn Glu Arg
    365                 370                 375

gcc gct cac atg aat gct caa ttc aga ttc taaggattta gttta            1261
Ala Ala His Met Asn Ala Gln Phe Arg Phe
380                 385


<210> SEQ ID NO 12
<211> LENGTH: 389
<212> TYPE: PRT
<213> ORGANISM: Chlamydia psittaci B577

<400> SEQUENCE: 12

Met Lys Lys Leu Leu Lys Ser Ala Leu Leu Phe Ala Ala Thr Gly Ser
 1               5                  10                  15
```

-continued

```
Ala Leu Ser Leu Gln Ala Leu Pro Val Gly Asn Pro Ala Glu Pro Ser
            20                  25                  30

Leu Leu Ile Asp Gly Thr Met Trp Glu Gly Ala Ser Gly Asp Pro Cys
        35                  40                  45

Asp Pro Cys Ser Thr Trp Cys Asp Ala Ile Ser Ile Arg Ala Gly Tyr
    50                  55                  60

Tyr Gly Asp Tyr Val Phe Asp Arg Val Leu Lys Val Asp Val Asn Lys
65                  70                  75                  80

Thr Ile Thr Gly Met Gly Ala Val Pro Thr Gly Thr Ala Ala Ala Asn
                85                  90                  95

Tyr Lys Thr Pro Thr Asp Arg Pro Asn Ile Ala Tyr Gly Lys His Leu
            100                 105                 110

Gln Asp Ala Glu Trp Phe Thr Asn Ala Ala Phe Leu Ala Leu Asn Ile
        115                 120                 125

Trp Asp Arg Phe Asp Ile Phe Cys Thr Leu Gly Ala Ser Asn Gly Tyr
    130                 135                 140

Phe Lys Ala Ser Ser Ala Ala Phe Asn Leu Val Gly Leu Ile Gly Val
145                 150                 155                 160

Lys Gly Ser Ala Met Ala Ala Asp Gln Leu Pro Asn Val Gly Ile Thr
                165                 170                 175

Gln Gly Ile Val Glu Phe Tyr Thr Asp Thr Thr Phe Ser Trp Ser Val
            180                 185                 190

Gly Ala Arg Gly Ala Leu Trp Glu Cys Gly Cys Ala Thr Leu Gly Ala
        195                 200                 205

Glu Phe Gln Tyr Ala Gln Ser Asn Pro Lys Ile Glu Met Leu Asn Val
    210                 215                 220

Val Ser Ser Pro Ala Gln Phe Val Val His Lys Pro Arg Gly Tyr Lys
225                 230                 235                 240

Gly Thr Ala Phe Pro Leu Pro Leu Thr Ala Gly Thr Asp Gln Ala Thr
                245                 250                 255

Asp Thr Lys Ser Ala Thr Ile Lys Tyr His Glu Trp Gln Val Gly Leu
            260                 265                 270

Ala Leu Ser Tyr Arg Leu Asn Met Leu Val Pro Tyr Ile Ser Val Asn
        275                 280                 285

Trp Ser Arg Ala Thr Phe Asp Ala Asp Ala Ile Arg Ile Ala Gln Pro
    290                 295                 300

Lys Leu Ala Ala Ala Val Leu Asn Leu Thr Thr Trp Asn Pro Thr Leu
305                 310                 315                 320

Leu Gly Glu Ala Thr Ala Leu Asp Thr Ser Asn Lys Phe Ala Asp Phe
                325                 330                 335

Leu Gln Ile Ala Ser Ile Gln Ile Asn Lys Met Lys Ser Arg Lys Ala
            340                 345                 350

Cys Gly Val Ala Val Gly Ala Thr Leu Ile Asp Ala Asp Lys Trp Ser
        355                 360                 365

Ile Thr Gly Glu Ala Arg Leu Ile Asn Glu Arg Ala Ala His Met Asn
    370                 375                 380

Ala Gln Phe Arg Phe
385
```

```
<210> SEQ ID NO 13
<211> LENGTH: 1660
<212> TYPE: DNA
<213> ORGANISM: Chlamydia psittaci 6BC
<220> FEATURE:
```

-continued

<221> NAME/KEY: CDS
<222> LOCATION: (364)...(1569)

<400> SEQUENCE: 13
ttacactctt ctacgagggt aattccaact tattctaagt ggcataagaa ataaaaatgt 60
gtacaaaaat ctgatagctc ttttattagc aagtataagg agttattgct tgaaatctat 120
gcctgaaaac agtctttttt cttatcgtct ttactataat aagaaaagtt tgttatgttt 180
tcgaataatg aactgtatgt tcatgcttaa ggctgttttc acttgcaaga cactcctcaa 240
agccattaat tgcctacagg atatcttgtc tggctttaac ttggacgtgg tgccgccaga 300
agagcaaatt agaatagcga gcacaaaaag aaaagatact aagcataatc tttagaggtg 360 agt atg aaa aaa ctc ttg aaa tcg gca tta ttg ttt gcc gct acg ggt 408
Met Lys Lys Leu Leu Lys Ser Ala Leu Leu Phe Ala Ala Thr Gly
1 5 10 15 tcc gct ctc tcc tta caa gcc ttg cct gta ggg aac cca gct gaa cca 456
Ser Ala Leu Ser Leu Gln Ala Leu Pro Val Gly Asn Pro Ala Glu Pro
20 25 30 agt tta tta atc gat ggc act atg tgg gaa ggt gct tca gga gat cct 504
Ser Leu Leu Ile Asp Gly Thr Met Trp Glu Gly Ala Ser Gly Asp Pro
35 40 45 tgc gat cct tgc gct act tgg tgt gac gcc att agc atc cgc gca gga 552
Cys Asp Pro Cys Ala Thr Trp Cys Asp Ala Ile Ser Ile Arg Ala Gly
50 55 60 tac tac gga gat tat gtt ttc gat cgt gta tta aaa gtt gat gtg aat 600
Tyr Tyr Gly Asp Tyr Val Phe Asp Arg Val Leu Lys Val Asp Val Asn
65 70 75 aaa act ttt agc ggc atg gct gca act cct acg cag gct aca ggt aac 648
Lys Thr Phe Ser Gly Met Ala Ala Thr Pro Thr Gln Ala Thr Gly Asn
80 85 90 95 gca agt aat act aat cag cca gaa gca aat ggc aga ccg aac atc gct 696
Ala Ser Asn Thr Asn Gln Pro Glu Ala Asn Gly Arg Pro Asn Ile Ala
100 105 110 tac gga agg cat atg caa gat gca gag tgg ttt tca aat gca gcc ttc 744
Tyr Gly Arg His Met Gln Asp Ala Glu Trp Phe Ser Asn Ala Ala Phe
115 120 125 cta gcc tta aac att tgg gat cgc ttc gac att ttc tgc acc tta ggg 792
Leu Ala Leu Asn Ile Trp Asp Arg Phe Asp Ile Phe Cys Thr Leu Gly
130 135 140 gca tcc aat gga tac ttc aaa gca agt tcg gct gca ttc aac ttg gtt 840
Ala Ser Asn Gly Tyr Phe Lys Ala Ser Ser Ala Ala Phe Asn Leu Val
145 150 155 ggg tta ata ggg ttt tca gct gca agc tca atc tct acc gat ctt cca 888
Gly Leu Ile Gly Phe Ser Ala Ala Ser Ser Ile Ser Thr Asp Leu Pro
160 165 170 175 atg caa ctt cct aac gta ggc att acc caa ggt gtt gtg gaa ttt tat 936
Met Gln Leu Pro Asn Val Gly Ile Thr Gln Gly Val Val Glu Phe Tyr
180 185 190 aca gac aca tca ttt tct tgg agc gta ggt gca cgt gga gct tta tgg 984
Thr Asp Thr Ser Phe Ser Trp Ser Val Gly Ala Arg Gly Ala Leu Trp
195 200 205 gaa tgt ggt tgt gca act tta gga gct gag ttc caa tac gct caa tct 1032
Glu Cys Gly Cys Ala Thr Leu Gly Ala Glu Phe Gln Tyr Ala Gln Ser
210 215 220 aat cct aag att gaa atg ctc aac gtc act tca agc cca gca caa ttt 1080
Asn Pro Lys Ile Glu Met Leu Asn Val Thr Ser Ser Pro Ala Gln Phe
225 230 235 gtg att cac aaa cca aga ggc tat aaa gga gct agc tcg aat ttt cct 1128
Val Ile His Lys Pro Arg Gly Tyr Lys Gly Ala Ser Ser Asn Phe Pro -continued

```
240                 245                 250                 255

tta cct ata acg gct gga aca aca gaa gct aca gac acc aaa tca gct      1176
Leu Pro Ile Thr Ala Gly Thr Thr Glu Ala Thr Asp Thr Lys Ser Ala
                260                 265                 270

aca att aaa tac cat gaa tgg caa gta ggc ctc gcc ctg tct tac aga      1224
Thr Ile Lys Tyr His Glu Trp Gln Val Gly Leu Ala Leu Ser Tyr Arg
            275                 280                 285

ttg aat atg ctt gtt cca tat att ggc gta aac tgg tca aga gca act      1272
Leu Asn Met Leu Val Pro Tyr Ile Gly Val Asn Trp Ser Arg Ala Thr
        290                 295                 300

ttt gat gct gat act atc cgc att gct caa cct aaa tta aaa tcg gag      1320
Phe Asp Ala Asp Thr Ile Arg Ile Ala Gln Pro Lys Leu Lys Ser Glu
    305                 310                 315

att ctt aac att act aca tgg aac cca agc ctt ata gga tca acc act      1368
Ile Leu Asn Ile Thr Thr Trp Asn Pro Ser Leu Ile Gly Ser Thr Thr
320                 325                 330                 335

gct ttg ccc aat aat agt ggt aag gat gtt cta tct gat gtc ttg caa      1416
Ala Leu Pro Asn Asn Ser Gly Lys Asp Val Leu Ser Asp Val Leu Gln
                340                 345                 350

att gct tcg att cag atc aac aaa atg aag tct aga aaa gct tgt ggt      1464
Ile Ala Ser Ile Gln Ile Asn Lys Met Lys Ser Arg Lys Ala Cys Gly
            355                 360                 365

gta gct gtt ggt gca acg tta atc gac gct gac aaa tgg tca atc act      1512
Val Ala Val Gly Ala Thr Leu Ile Asp Ala Asp Lys Trp Ser Ile Thr
        370                 375                 380

ggt gaa gca cgc tta atc aat gaa aga gct gct cac atg aat gct caa      1560
Gly Glu Ala Arg Leu Ile Asn Glu Arg Ala Ala His Met Asn Ala Gln
    385                 390                 395

ttc aga ttc taaggattta gtttatacta tcctaacttt ttaaaccgct             1609
Phe Arg Phe
400

atcagaacct gggagtctcc gggttctgat tttttaaata ccaccctttt c             1660


<210> SEQ ID NO 14
<211> LENGTH: 402
<212> TYPE: PRT
<213> ORGANISM: Chlamydia psittaci 6BC

<400> SEQUENCE: 14

Met Lys Lys Leu Leu Lys Ser Ala Leu Leu Phe Ala Ala Thr Gly Ser
 1               5                  10                  15

Ala Leu Ser Leu Gln Ala Leu Pro Val Gly Asn Pro Ala Glu Pro Ser
            20                  25                  30

Leu Leu Ile Asp Gly Thr Met Trp Glu Gly Ala Ser Gly Asp Pro Cys
        35                  40                  45

Asp Pro Cys Ala Thr Trp Cys Asp Ala Ile Ser Ile Arg Ala Gly Tyr
    50                  55                  60

Tyr Gly Asp Tyr Val Phe Asp Arg Val Leu Lys Val Asp Val Asn Lys
65                  70                  75                  80

Thr Phe Ser Gly Met Ala Ala Thr Pro Thr Gln Ala Thr Gly Asn Ala
                85                  90                  95

Ser Asn Thr Asn Gln Pro Glu Ala Asn Gly Arg Pro Asn Ile Ala Tyr
            100                 105                 110

Gly Arg His Met Gln Asp Ala Glu Trp Phe Ser Asn Ala Ala Phe Leu
        115                 120                 125

Ala Leu Asn Ile Trp Asp Arg Phe Asp Ile Phe Cys Thr Leu Gly Ala
    130                 135                 140
```

-continued

Ser Asn Gly Tyr Phe Lys Ala Ser Ser Ala Ala Phe Asn Leu Val Gly
145 150 155 160

Leu Ile Gly Phe Ser Ala Ala Ser Ser Ile Ser Thr Asp Leu Pro Met
165 170 175

Gln Leu Pro Asn Val Gly Ile Thr Gln Gly Val Val Glu Phe Tyr Thr
180 185 190

Asp Thr Ser Phe Ser Trp Ser Val Gly Ala Arg Gly Ala Leu Trp Glu
195 200 205

Cys Gly Cys Ala Thr Leu Gly Ala Glu Phe Gln Tyr Ala Gln Ser Asn
210 215 220

Pro Lys Ile Glu Met Leu Asn Val Thr Ser Ser Pro Ala Gln Phe Val
225 230 235 240

Ile His Lys Pro Arg Gly Tyr Lys Gly Ala Ser Ser Asn Phe Pro Leu
245 250 255

Pro Ile Thr Ala Gly Thr Thr Glu Ala Thr Asp Thr Lys Ser Ala Thr
260 265 270

Ile Lys Tyr His Glu Trp Gln Val Gly Leu Ala Leu Ser Tyr Arg Leu
275 280 285

Asn Met Leu Val Pro Tyr Ile Gly Val Asn Trp Ser Arg Ala Thr Phe
290 295 300

Asp Ala Asp Thr Ile Arg Ile Ala Gln Pro Lys Leu Lys Ser Glu Ile
305 310 315 320

Leu Asn Ile Thr Thr Trp Asn Pro Ser Leu Ile Gly Ser Thr Thr Ala
325 330 335

Leu Pro Asn Asn Ser Gly Lys Asp Val Leu Ser Asp Val Leu Gln Ile
340 345 350

Ala Ser Ile Gln Ile Asn Lys Met Lys Ser Arg Lys Ala Cys Gly Val
355 360 365

Ala Val Gly Ala Thr Leu Ile Asp Ala Asp Lys Trp Ser Ile Thr Gly
370 375 380

Glu Ala Arg Leu Ile Asn Glu Arg Ala Ala His Met Asn Ala Gln Phe
385 390 395 400

Arg Phe

<210> SEQ ID NO 15
<211> LENGTH: 26
<212> TYPE: DNA
<213> ORGANISM: Artificial Sequence
<220> FEATURE:
<223> OTHER INFORMATION: primer 5GPF

<400> SEQUENCE: 15
acgcatgcaa gacactcctc aaagcc 26

<210> SEQ ID NO 16
<211> LENGTH: 28
<212> TYPE: DNA
<213> ORGANISM: Artificial Sequence
<220> FEATURE:
<223> OTHER INFORMATION: primer 3GPB

<400> SEQUENCE: 16
acgaattcct aggttctgat agcgggac 28

<210> SEQ ID NO 17
<211> LENGTH: 27
<212> TYPE: DNA
<213> ORGANISM: Artificial Sequence -continued

```
<220> FEATURE:
<223> OTHER INFORMATION: primer cBamA

<400> SEQUENCE: 17

cggatccatt acccaaggtg ttatgga                                         27


<210> SEQ ID NO 18
<211> LENGTH: 21
<212> TYPE: DNA
<213> ORGANISM: Artificial Sequence
<220> FEATURE:
<223> OTHER INFORMATION: primer ParaBamG

<400> SEQUENCE: 18

taaaggatcc gccatggcag c                                               21
```

VACCINES FOR *CHLAMYDIA PSITTACI* INFECTIONS

This application claims priority in Provisional Patent Application Serial No. 60/057,147, filed on Aug. 28, 1997.

BACKGROUND OF THE INVENTION

1. Field of the Invention

The present invention relates to *Chlamydia psittaci* vaccines and to methods of protecting animals, including avian species, from *Chlamyida psittaci* infections.

2. Background Art

The genus Chlamydia contains four species of obligate parasitic bacteria: *Chlamydia psittaci, Chlamydia pecorum, Chlamydia pneumoniae*, and *Chlamydia trachomatis*. This unique genus causes a variety of diseases in humans, mammals, and birds. In humans, the most notable are trachoma and urogenital infections due to *C. trachomatis* and psittacosis caused by *C. psittaci*. In animals, *C. psittaci* can cause a diverse range of disease in livestock, poultry, turkeys and companion birds. The known *C. psittaci* strains have been grouped into eight biovars (Perez-Martinez, J A and J Storz, 1985). Strains of serovar 1 are mainly associated with intestinal infections and abortions, while strains of serovar 2 cause polyarthritis, encephalitis, and conjunctivitis in ruminants. Avian strains of *C. psittaci* cause respiratory problems and diarrhea in birds (Storz, 1988). The organism can also be transmitted to humans from these animals, and outbreaks have been documented in animal production workers. Thus, there is a need for an effective vaccine against *C. psittaci* for mammalian and avian species.

The chlamydia organism goes through two developmental stages in its life cycle. The extracellular form, which is the infectious entity of the cycle, is called the elementary body (EB). These EBs attach and enter the host cell, where they re-organize into reticulate bodies (RBs) which divide within membrane-bound host cell compartments by binary fission and then condense into a new generation of infectious EBs. The attachment and entry of the EB into the host cell is a receptor-mediated phenomenon (Hodinka et al. 1988), and several chlamydial proteins have been implicated in the EB attachment to host cellular membranes (Baghian and Schnorr, 1992). One of these proteins is called the "major outer membrane protein", or MOMP, and surface-exposed epitopes of this protein from *C. trachomatis* have been shown to block EB attachment onto the host cell (Su and Caldwell, 1991). The MOMP genes from some strains of *C. psittaci* and *C. trachomatis* have been sequenced (Baehr et al., 1988, Pickett et al. 1988, Yuan et al. 1989, Zhang et al. 1989, Kaltenboeck, et al. 1993). Analyses of these sequences revealed that portions of the structure of this protein are conserved between species. There are also four regions of "variable domain" interspersed with conserved sequences, and these are referred to as VD1, VD2, VD3, and VD4. The location of these VD regions are identical in the two species (see Zhang et al., 1989). A comparison of the genes encoding the MOMP from *C. psittaci* and *C. trachomatis* show that, overall, the sequences are approximately 68% identical.

In *C. trachomatis*, these four variable regions have been shown to be involved in the neutralization of EB infectivity, in serotype specificity, (Baehr, et al. 1988; Peeling et al. 1984; and Spears and Storz 1979) as well as in the pathogenicity of the strains (Baehr et al. 1988 and Su et al. 1988). Nonetheless, the development of subunit vaccines for *C. trachomatis* has been hampered by the difficulty in expressing the native, full-length MOMP gene in a recombinant vector host (Manning and Stewart, 1993). There is no known published work on the expression of the *C. psittaci* MOMP gene prior to that described herein. Consequently, there remains a need to develop an effective subunit vaccine for animal and avian species to protect them from *C. psittaci* infections.

SUMMARY OF THE INVENTION

The present invention provides a vaccine composition which is protective against *Chlamydia psittaci* infections in animals, including avian species, comprising an immunogenic amount of a *C. psittaci* major outer membrane protein (MOMP) polypeptide lacking regions VD1 and VD2. Also provided are polypeptides and isolated nucleic acids encoding such polypeptides, as well as methods of preventing *C. psittaci* infections in animals comprising administering to the subject animal such vaccine compositions.

Also provided are nucleic acid vectors for the expression of a MOMP polypeptide-MBP fusion protein comprising a nucleic acid encoding MBP and a nucleic acid encoding an immunogenic *C. psittaci* MOMP polypeptide arranged in tandem such that the MOMP-MBP fusion protein can be expressed.

Additionally provided are methods of preventing a *Chlamydia psittaci* infection in a subject comprising administering to the subject a nucleic acid vaccine comprising an immunizing amount of a nucleic acid vector comprising a nucleic acid encoding an immunogenic *C. psittaci* MOMP polypeptide lacking regions VD1 and VD2.

DETAILED DESCRIPTION OF THE INVENTION

Definitions

"MOMP" means the major outer membrane protein from a *Chlamydia psittaci* strain.

As used herein, the term "polypeptide" refers to a polymer of amino acids. As used in combination with MOMP, it means a fragment of MOMP.

As used in the specification and in the claims, "a" can mean one or more, depending upon the context in which it is used.

Maltose Binding Protein, or "MBP" means a maltose binding protein.

The term "immunogenic amount" means an amount of an immunogen, i.e., a MOMP polypeptide, a MOMP polypeptide-MBP fusion protein, or portions thereof, which is sufficient to induce an immune response in a vaccinated animal and which protects the animal against active infection with *Chlamydia psittaci* upon exposure thereto.

The term "immunizing amount" means an amount of a nucleic acid expression vector sufficient to induce an immune response in a vaccinated animal and which protects the animal against active infection with *Chlamydia psittaci* upon exposure thereto.

Detailed Description

Vaccine preparations that are efficacious and economical for use in human and non-human animals, including birds, such as chickens, turkeys and companion birds, are provided.

Polypeptide Vaccines

The present invention provides a vaccine composition which is protective against *Chlamydia psittaci* infections in animals, including avian species, comprising an immunogenic amount of a *C. psittaci* major outer membrane protein (MOMP) polypeptide lacking variable regions VD1 and VD2. In specific embodiments, the vaccine composition can comprise an immunogenic amount of a *C. psittaci* major outer membrane protein (MOMP) polypeptide comprising amino acids 183 through 402 of the MOMP protein from *C. psittaci* strains Avian Type C, LSUWTCK (a strain isolated from a cockatiel which has the identical MOMP gene sequence to Avian Type C), or strain 6BC (which is identical to the sequence of Mn except for a single amino acid change), or amino acids 164 to 389 of the MOMP protein from *C. psittaci* strain B577.

The complete nucleic acid sequences of the MOMP gene from *C. psittaci* strains Avian Type C, B577, and 6BC are provided herein as SEQ ID NO: 9, SEQ ID NO: 11 and SEQ ID NO: 13, respectively, and the corresponding amino acid sequences of the MOMP proteins are provided herein as SEQ ID NO: 10, SEQ ID NO: 12, and SEQ ID NO: 14, respectively.

The MOMP polypeptide is purified from other proteins sufficiently to induce a specific immune response. Thus, in specific embodiments, the MOMP polypeptide comprising the vaccine comprises the amino acid sequence set forth in SEQ ID NO:1. In another embodiment, the MOMP polypeptide of the vaccine comprises the amino acid sequence set forth in SEQ ID NO:2.

In a specific embodiment of this invention, the MOMP polypeptide is provided as a component of a fusion protein. Thus the present invention provides a vaccine composition comprising a MOMP polypeptide, as described herein, linked to a non-MOMP polypeptide or protein, and a nucleic acid encoding such a fusion protein. A MOMP fusion protein can be made with any desired protein as part of the chimera. One example is glutathione-S-transferase ("GST") which is commonly used as a fusion protein. Another example is Maltose Binding Protein (MBP). Thus, in one embodiment, a vaccine composition comprises a Maltose Binding Protein-MOMP fusion protein, wherein the MOMP portion of the fusion protein is a *C. psittaci* MOMP polypeptide. Such a fusion protein can have MBP as the amino terminal protein of the fusion protein and the MOMP polypeptide as the carboxyl terminal portion of the fusion protein. Specifically provided is a vaccine composition comprising an MBP-MOMP fusion protein which includes the polyamino acid encoded by nucleotides 1606–2661 of the MBP sequence from the *E. coli* malE gene (available, for example, in the vector pMAL™-c2 from New England Biolabs, Inc., Beverly, Mass. 01915-5999). Also specifically provided is a vaccine composition comprising MBP-MOMP fusion protein wherein the MOMP polypeptide is a *C. psittaci* MOMP polypeptide comprising amino acids 183 through 402 of the MOMP protein from either *C. psittaci* strains Avian Type C, LSUWTCK, or 6BC, or amino acids 164 to 389 of the MOMP protein from *C. psittaci* strain B577. Fusion proteins utilizing MBP sequences are presented in U.S. Pat. No. 5,643,758. The fusion protein of this invention has several advantageous characteristics. The unexpected discovery that such a MBP-MOMP fusion protein precipitates in inclusion bodies in the bacterial host cells provided an economical method for purifying this immunogen. Specifically, for example, this MBP-MOMP fusion protein can be expressed from a nucleic acid encoding it in relatively large amounts (e.g., 100 milligrams per liter of *E.coli*) in a manner such that the fusion protein can be very easily purified to a useful extent. Typically, MBP-protein fusions are purified by passing the cell extract over an affinity column bound with an appropriate ligand for MBP. The added cost of such a preparation step generally makes such proteins uneconomical as vaccines in production animals. The MBP-MOMP fusion protein of this invention can be prepared to sufficient purity without the use of such a column, making the economical production of a production or companion animal vaccine possible. This MBP-MOMP fusion protein precipitates as inclusion bodies, and thus traditional purification techniques, such as affinity columns, are not necessary, and the resulting purified fusion protein retains immunogenicity.

Polypeptides having amino acid substitutions from the sequences set forth, that do not significantly reduce the immunogenicity of the polypeptides, are contemplated by this invention. For example, amino acid substitutions can be selected by known parameters to be neutral substitutions (see, e.g., Robinson W E Jr, and Mitchell W M., AIDS 4:S151–S162(1990)). As will be appreciated by those skilled in the art, the invention also includes those polypeptides having slight variations in amino acid sequences or other properties. Such variations may arise naturally as allelic variations (e.g., due to genetic polymorphism) or may be produced by human intervention (e.g., by mutagenesis of cloned DNA sequences), such as induced point, deletion, insertion and substitution mutants. Minor changes in amino acid sequence are generally preferred, such as conservative amino acid replacements, small internal deletions or insertions, and additions or deletions at the ends of the molecules. Substitutions may be designed based on, for example, the model of Dayhoff, et al. (in *Atlas of Protein Sequence and Structure* 1978, Nat'l Biomed. Res. Found., Washington, D.C.). These modifications can result in changes in the amino acid sequence, provide silent mutations, modify a restriction site, or provide other specific mutations. Additionally, the amino acid sequences of the MOMP polypeptide vaccines of this invention can include sequences in which one or more amino acids have been substituted with another amino acid to provide for some additional property, such as to remove/add amino acids capable of disulfide bonding, to increase its bio-longevity, alter enzymatic activity, or alter interactions with gastric acidity. In any case, the peptide must retain *C. psittaci*—protective immunogenicity.

It is also contemplated in this invention that the variable regions VD3 and VD4 can be administered either in the form of a single MOMP polypeptide, for example SEQ ID NO:1 or SEQ ID NO:2, or as multiple MOMP polypeptides, each one encoding one of the variable regions. Techniques for producing such MOMP polypeptides are routine in art, given the knowledge of the full DNA sequence of the MOMP genes. For example, one can construct multiple nucleic acid vectors by first enzymatically cleaving the DNA of the MOMP gene at restriction enzyme sites located on either side and between variable regions VD3 and VD4 and then cloning the resulting DNA fragments into appropriate vectors for expression. Alternatively, as shown in the Examples herein, artificial primers can be designed to amplify the desired portions of the MOMP gene with convenient restriction enzyme recognition sites in the primers, to allow rapid and efficient cloning of selected portions of the MOMP gene into expression vectors.

Selected MOMP polypeptides can be assayed for immunogenicity and specificity. Briefly, various concentrations of a putative immunogenically specific polypeptide are prepared and administered to an animal and the immunological response (e.g., the production of antibodies or cell mediated immunity) of an animal to each concentration is determined. The amounts of antigen administered depend on the subject, e.g. a human or a non-human animal, including a bird, the condition of the subject, the size of the subject, etc. Thereafter an animal so inoculated with the antigen can be exposed to the bacterium to test the potential vaccine effect of the specific immunogenic MOMP polypeptide. The specificity of a putative immunogenic MOMP polypeptide can be ascertained by testing sera, other fluids or lymphocytes from the inoculated animal for cross-reactivity with other closely related bacteria. Nucleic acids The present invention provides an isolated nucleic acid comprising a nucleic acid which encodes a *C. psittaci* MOMP polypeptide lacking VD1 and VD2. In a specific embodiment, the nucleic acid includes the variable regions VD3 and VD4 (e.g., amino acids 183 to 402 of the *C. psittaci* Avian Type C, LSUWTCK, or 6BC MOMP protein, or amino acids 162 to 389 of the *C. psittaci* B577 MOMP protein. Additionally, the amino terminus end of the isolated nucleic acid can be modified from the native sequence to include an ATG (methionine) start codon and a Kozak regulatory sequence, both of which are typically required for translation in eukaryotes.

In a specific embodiment, the present invention provides an isolated nucleic acid comprising a nucleic acid having the nucleotide sequence set forth in SEQ ID NO:3. This nucleic acid encodes roughly the carboxyl-terminal half of the *C. psittaci* strain Avian Type C MOMP protein and includes VD3 and VD4. Additionally, the amino terminus end of this sequence has been modified from the native sequence to include an ATG (methionine) start codon and a Kozak regulatory sequence. Another embodiment of this invention provides an isolated nucleic acid having the nucleotide sequence set forth in SEQ ID NO: 4, which ends at the stop codon TAA, and thus does not include the 3' untranslated sequences included in SEQ ID NO:3.

In another embodiment, the present invention provides an isolated nucleic acid comprising a nucleic acid having the nucleotide sequence set forth in SEQ ID NO: 5. This nucleic acid encodes roughly the carboxyl-terminal half of the *C. psittaci* strain B577 MOMP protein and includes VD3 and VD4, and additionally has an ATG (methionine) and a Kozak consensus sequence at the amino terminus of this polypeptide. Another embodiment of this invention provides an isolated nucleic acid having the nucleotide sequence set forth in SEQ ID NO: 6, which ends at the stop codon TAA, and thus does not include the 3' untranslated sequences included in SEQ ID NO:5.

The present invention also provides a composition which is protective against *C. psittaci* infections comprising polypeptides expressed in a suitable host by one or more of the isolated nucleic acids of this invention and a pharmaceutically acceptable carrier.

Also provided is a nucleic acid vector for the expression of a MOMP polypeptide-MBP fusion protein comprising a nucleic acid encoding MBP and a nucleic acid encoding a MOMP polypeptide arranged in tandem such that the MOMP-MBP fusion protein can be expressed. In a specific embodiment, the nucleic acid encodes an amino acid sequence for the MOMP polypeptide selected from the group consisting of: SEQ ID NO:1 and SEQ ID NO:2. In a preferred embodiment, the nucleic acid encoding MBP is located 5' to the nucleic acid encoding MOMP. Persons skilled in the art are knowledgeable in arranging the nucleic acids such that the fusion protein can be expressed, including ensuring that the reading frame for both nucleic acids is the same, and including various control regions, as also further discussed herein.

In another embodiment, the present invention provides a nucleic acid vector for the transient expression of a *C. psittaci* MOMP polypeptide in a eukaryotic cell comprising a eukaryotic promoter functionally linked to a nucleic acid encoding a *C. psittaci* MOMP polypeptide lacking regions VD1 and VD2. In a specific embodiment, the nucleic acid encodes an amino acid sequence selected from the group consisting of: SEQ ID NO:7 or SEQ ID NO:8. In a further specific embodiment, the nucleic acid has a sequence selected from the group consisting of: SEQ ID NO:3, SEQ ID NO:4, SEQ ID NO:5 and SEQ ID NO:6. Any desired eukaryotic promoter can be utilized; however, preferable promoters are those that are strong promoters in avian or mammalian cells, as are known in the art and further described below. As discussed herein, certain modifications to the nucleic acid vectors can be made.

In a specific embodiment, provided herein is a nucleic acid vector for the transient expression of a *C. psittaci* MOMP polypeptide in a eukaryotic cell comprising a cytomegalovirus promoter functionally linked to a nucleic acid encoding a *C. psittaci* MOMP polypeptide lacking regions VD1 and VD2. In a further specific embodiment, the nucleic acid encodes an amino acid sequence selected from the group consisting of: SEQ ID NO:7 and SEQ ID NO:8.

Nucleic Acid Vaccines

The present invention provides compositions comprising a plurality of the nucleic acid vectors for the transient expression of a *C. psittaci* MOMP polypeptide in a eukaryotic cell comprising a eukaryotic promoter functionally linked to a nucleic acid encoding amino acid sequence comprising a *C. psittaci* major outer membrane protein (MOMP) polypeptide lacking regions VD1 and VD2. Such compositions ate administered to a subject such that they can be expressed in the subject, the "plurality" of vectors being sufficient to induce an immune response.

In a specific embodiment, the present invention provides a composition which is protective against a *Chlamydia psittaci* infection in animals, including avian species, comprising a plurality of nucleic acid expression vectors comprising a eukaryotic promoter functionally linked to a nucleic acid encoding the amino acid sequence set forth in SEQ ID NO:7 or SEQ ID NO:8 in a pharmaceutically acceptable carrier.

In a further specific embodiment, the present invention provides a composition which is protective against *Chlamydia psittaci* infections in animals, including avian species, comprising a plurality of nucleic acid expression vectors comprising a eukaryotic promoter functionally linked to one or more nucleotide sequences selected from the group consisting of: SEQ ID NO:3, SEQ ID NO:4, SEQ ID NO:5 and SEQ ID NO:6 in a pharmaceutically acceptable carrier.

In a specific embodiment, the nucleic acid expression vector comprises a cytomegalovirus promoter functionally linked to a nucleic acid encoding VD3 and VD4 of MOMP, for example having the nucleotide sequence set forth in either SEQ ID NO:3, SEQ ID NO:4, SEQ ID NO:5 or SEQ ID NO:6.

Nucleic Acids/Vectors/Vaccines-general

The nucleic acid encoding the MOMP polypeptide can be any nucleic acid that functionally encodes the MOMP polypeptide. For example, to functionally encode, i.e., allow the nucleic acid to be expressed, the nucleic acid can include, for example, expression control sequences, such as an origin of replication, a promoter, an enhancer, and necessary information processing sites, such as ribosome binding sites, RNA splice sites, polyadenylation sites, and transcriptional terminator sequences. Preferred expression control sequences are strong and/or inducible promoters such as those derived from metallothionine genes, actin genes, immunoglobulin genes, CMV, SV40, Rous sarcoma virus, adenovirus, bovine papilloma virus, etc. A nucleic acid encoding a selected MOMP polypeptide can readily be determined based upon the genetic code for the amino acid sequence of the selected MOMP polypeptide, and, clearly, many nucleic acids will encode any selected chimeric protein. Modifications to the nucleic acids of the invention are also contemplated, since mutations can thereby be studied for greater protective vaccine effect. Additionally, modifications that can be useful are modifications to the sequences controlling expression of the MOMP polypeptide to make production of the MOMP polypeptide inducible or repressible upon addition to the cells of the appropriate inducer or repressor. Such means are standard in the art (see, e.g.,. Sambrook et al., *Molecular Cloning: A Laboratory Manual,* 2nd Ed., Cold Spring Harbor Laboratory, Cold Spring Harbor, N.Y., 1989). The nucleic acids can be generated by means standard in the art, such as by recombinant nucleic acid techniques, as exemplified in the examples herein, and by synthetic nucleic acid synthesis or in vitro enzymatic synthesis.

The expression vectors of the invention can be in a host capable of expressing the MOMP polypeptide immunogen or the MBP-MOMP fusion protein immunogen. There are numerous *E. coli* expression vectors known to one of ordinary skill in the art useful for the expression of the antigen. Other microbial hosts suitable for use include bacilli, such as *Bacillus subtilus*, and other enterobacteriaceae, such as Salmonella, Serratia, and various Pseudomonas species. In these prokaryotic hosts one can also make expression vectors, which will typically contain expression control sequences compatible with the host cell (e.g., an origin of replication). In addition, any number of a variety of well-known promoters will be present, such as the lactose promoter system, a tryptophan (Trp) promoter system, a beta-lactamase promoter system, or a promoter system from phage lambda. The promoters will typically control expression, optionally with an operator sequence, and have ribosome binding site sequences for example, for initiating and completing transcription and translation. If necessary an amino terminal methionine can be provided by insertion of a Met codon 5' and in-frame with the antigen. Also, the carboxyl-terminal extension of the antigen can be removed using standard oligonucleotide mutagenesis procedures.

Additionally, yeast expression systems can be used. There may be several advantages to yeast expression systems. First, evidence exists that proteins produced in a yeast secretion systems exhibit correct disulfide pairing. Second, post-translational glycosylation is efficiently carried out by yeast secretory systems. The *Saccharomyces cerevisiae* pre-pro-alpha-factor leader region (encoded by the MF $\alpha$-1 gene) is routinely used to direct protein secretion from yeast (Brake et al., 1984). The leader region of pre-pro-alpha-factor contains a signal peptide and a pro-segment which includes a recognition sequence for a yeast protease encoded by the KEX2 gene: this enzyme cleaves the precursor protein on the carboxyl side of a Lys-Arg dipeptide cleavage-signal sequence. The antigen coding sequence can be fused in-frame to the pre-pro-alpha-factor leader region. This construct is then put under the control of a strong transcription promoter, such as the alcohol dehydrogenase I promoter or a glycolytic promoter. The antigen coding sequence is followed by a translation termination codon which is followed by transcription termination signals. Alternatively, the antigen coding sequences can be fused to a second protein coding sequence, such as Sj26 or $\beta$-galactosidase, used to facilitate purification of the fusion protein by affinity chromatography. The insertion of protease cleavage sites to separate the components of the fusion protein is applicable to constructs used for expression in yeast.

Additionally, mammalian cells permit the expression of proteins in an environment that favors important post-translational modifications such as folding and cysteine pairing, addition of complex carbohydrate structures, and secretion of active protein. Vectors useful for the expression of antigen in mammalian cells are characterized by insertion of the antigen coding sequence between a strong viral promoter and a polyadenylation signal. The vectors can contain genes conferring either gentamicin or methotrexate resistance for use as selectable markers. The antigen and immunoreactive fragment coding sequence can be introduced into a Chinese hamster ovary cell line using a methotrexate resistance-encoding vector. Presence of the vector DNA in transformed cells can be confirmed by Southern analysis and production of an RNA corresponding to the antigen coding sequence can be confirmed by Northern analysis. A number of other suitable host cell lines capable of secreting intact human proteins have been developed in the art, and include the CHO cell lines, HeLa cells, myeloma cell lines, Jurkat cells, etc. Expression vectors for these cells can include expression control sequences, such as an origin of replication, a promoter, an enhancer, and necessary information processing sites, such as ribosome binding sites, RNA splice sites, polyadenylation sites, and transcriptional terminator sequences. Preferred expression control sequences are promoters derived from immunoglobulin genes, SV40, Adenovirus, Bovine Papilloma Virus, etc. The vectors containing the DNA segments of interest can be transferred into the host cell by well-known methods, which vary depending on the type of cellular host. For example, calcium chloride transfection is commonly utilized for prokaryotic cells, whereas calcium phosphate treatment or electroporation may be used for other cellular hosts.

Alternative vectors for the expression of antigen in mammalian cells, those similar to those developed for the expression of human gamma-interferon, tissue plasminogen activator, clotting Factor VIII, hepatitis B virus surface antigen, protease Nexinl, and eosinophil major basic protein, can be employed. Further, the vector can include cytomegalovirus (CMV) promoter sequences and a polyadenylation signal available for expression of inserted DNAs in mammalian cells.

The nucleic acid vectors for transient expression in a eukaryotic cell are suitable for genetic, or "naked nucleic acid", immunization. These can be constructed using any of a variety of eukaryotic promoters, herein also referred to as cis-acting transcription/translation regulatory sequences, known in the art. General methods for the construction, production and administration of nucleic acid vaccines are known in the art, e.g. Vogel, FR and N Sarver (1995) *Clin. Microbiol. Rev.* 8:406–410.

These nucleic acid vectors comprise nucleic acids that functionally encode, i.e. are functionally linked to a nucleic acid encoding a MOMP polypeptide. For example, to functionally encode, i.e., allow the nucleic acid to be expressed, the nucleic acid can include, for example, expression control sequences, such as a cis-acting transcription/translation regulatory sequence (comprising one or more of the following: a promoter, response element(s), an initiator sequence), an enhancer, and information processing sites, such as ribosome binding sites, RNA splice sites, intron elements, polyadenylation sites, and transcriptional terminator sequences, all of which, either alone or in combinations, are capable of directing expression in the target animal. Preferred expression control sequences are strong and/or inducible cis-acting transcription/translation regulatory sequences such as those derived from metallothionine genes, actin genes, myosin genes, immunoglobulin genes, cytomegalovirus (CMV), SV40, Rous sarcoma virus, adenovirus, bovine papilloma virus, etc. The *C. psittaci* MOMP-encoding nucleic acid and expression control sequences are constructed in a vector, such as a plasmid of bacterial origin, for administration to the target animal. There are numerous plasmids known to those of ordinary skill in the art useful for the production of nucleic acid vaccine plasmids. A specific embodiment employs constructs using the plasmid "pcDNA3.1$^{+}$" as the vector (InVitrogen Corporation, Carlsbad, Calif.). In addition, the nucleic acid expression vectors that functionally encode a MOMP polypeptide may additionally contain immunostimulatory sequences ("ISS") that stimulate the animals' immune system. Other possible additions to the nucleic acid expression vectors include nucleic acid sequences encoding cytokines, such as granulocyte macrophage colony stimulating factor (GM-CSF) or interleukin-12 (IL-12). The cytokines can be used in various combinations to fine-tune the response of the animal's immune system, including both antibody and cytotoxic T lymphocyte responses, to bring out the specific level of response needed to protect the animal from the targeted disease.

Alternatively, the nucleic acid expression vectors can be constructed in a non-replicating retroviral vector, such as the Moloney murine leukemia virus (N2) backbone described by Irwin, et al. (1994, J. Virology 68:5036–5044).

The present genes were isolated from *C. psittaci*; however, homologs from any Chlamydia strain infecting a selected species, can readily be obtained by screening a library from that Chlamydia strain, genomic or cDNA, with a probe comprising sequences of the nucleic acids set forth in the sequence listing herein, or fragments thereof, and isolating genes specifically hybridizing with the probe under preferably relatively high stringency hybridization conditions. For example, high salt conditions and/or high temperatures of hybridization can be used. For example, the stringency of hybridization is typically about 5° C. to 20° C. below the $T_m$ (the melting temperature at which half of the molecules dissociate from its partner) for the given chain length. As is known in the art, the nucleotide composition of the hybridizing region factors in determining the melting temperature of the hybrid. For 20mer probes, for example, the recommended hybridization temperature is typically about 55–58° C. Additionally, the *C. psittaci* MOMP sequence can be utilized to devise a probe for a homolog in any specific animal by determining the amino acid sequence for a portion of the *C. psittaci* protein, and selecting a probe with optimized codon usage to encode the amino acid sequence of the homolog in that particular animal.

The present invention contemplates cells containing a nucleic acid expression vector of the invention. A cell containing a nucleic acid expression vector encoding a MOMP polypeptide typically can replicate the DNA and, further, typically can express the encoded MOMP polypeptide. The cell can be a prokaryotic cell, particularly for the purpose of producing quantities of the nucleic acid, or a eukaryotic cell, particularly a mammalian cell. The cell is preferably a mammalian cell for the purpose of expressing the encoded protein so that the resultant produced protein has mammalian protein processing modifications. The cell also can be a eukaryotic cell in a host organism, for the purposes of vaccinating the host via genetic or "naked nucleic acid" immunization. In the case of genetic immunization, the nucleic acid expression vector does not typically replicate in the host.

In one embodiment, a nucleic acid expression vector of this invention is administered in combination with one or more other nucleic acid vectors, as a "naked nucleic acid immunization" to protect against multiple viral diseases. In a specific embodiment for vaccinating birds, the other viral diseases can be avian polyomavirus, Pacheco's disease virus, or psittacine beak and feather disease virus.

In another specific embodiment, the vaccine composition comprising an immunogenic amount of a *C. psittaci* major outer membrane protein (MOMP) polypeptide lacking variable regions VD1 and VD2 is administered in combination with one or more recombinant viral proteins from viruses that infect and cause disease in psittacine birds.

Any vaccine composition of this invention can further comprise an adjuvant suitable for use in the species to which the vaccine is to be administered, such as avian or mammalian species. Examples of such adjuvants include but are not limited to a cytokine, such as a lymphokine, a monokine or a chemokine, or a cytokine inducer or an agent that facilitates the entry of the antigen into the cytoplasm of the cell. Other examples of adjuvants that can useful in the present invention include but are not limited to plasmid DNA or bacterial agents. An adjuvant can also include, for example, immunomodulators and co-stimulatory molecules. Additional adjuvants include any compound described in Chapter 7 (pp 141–227) of 'Vaccine Design, The Subunit and Adjuvant Approach' (eds. Powell, M. F. and Newman, M. J.) Pharmaceutical Biotechnology, Volume 6, Plenum Press (New York).

Any vaccine composition of this invention can further comprise a pharmaceutically acceptable carrier. By "pharmaceutically acceptable" is meant a material that is not biologically or otherwise undesirable, i.e., the material may be administered to an individual along with the selected compound without causing any undesirable biological effects or interacting in a deleterious manner with any of the other components of the pharmaceutical composition in which it is contained. A pharmaceutically acceptable carrier can comprise saline or other suitable carriers (Arnon, R., (Ed.) Synthetic Vaccines 1:83–92; CRC Press, Inc., Boca Raton, Fla. 1987).

Methods of Vaccination

The present invention further provides methods of vaccinating a subject to induce an immunological response capable of preventing a subsequent *C. psittaci* infection. The vaccine can be administered to an animal of the avian species, such as poultry, turkeys and companion birds; additionally, particularly for handlers of such avian species, the vaccines can be administered to mammals such as humans. In particular, birds which can be treated by the invention can be any of the various species of birds which are classified as being members of the Psittaciformes order. Examples of such birds include, but are not limited to, Budgerigars (*Melopsittacus undulatus*), caiques (e.g., *Pionites leucogaster leucogaster*), macaws (e.g., *Ara ararauna*), Amazon parrots (e.g., *Amazona ochrocephala auropalliata,* conures (e.g., *Pyrrhara picta, Aratinga wagleri wagleri, Aratinga solstitialis, Aratinga guarouba, Aratinga holochlora rubritorquis* or *Aratinga acuticaudata acuticaudata*), cockatoos (e.g., *Cacatua moluccensis, Cacatua ducorps, Cacatua sulphura, Cacatua goffini* or *Cacatua alba*), Splendid Parakeets (*Neophema splendida*), Pionus Parrots (*Pionus maximillani*), African Grey Parrots (*Psittacus erithacus erithacus*, Eclectus Parrots (*Electus roratus*), Cockatiels (*Nymphicus hollandicus*) and parakeets (e.g. *Psittacula krameri krameri*).

Thus, the present invention provides a method of preventing a *Chlamydia psittaci* infection in a subject comprising administering to the subject a vaccine comprising an immunogenic amount of a *C. psittaci* major outer membrane protein (MOMP) polypeptide lacking variable regions VD1 and VD2. In a specific embodiment, the method comprises an immunogenic amount of a MOMP polypeptide having an amino acid sequence as set forth in either SEQ ID NO:1 or SEQ ID NO:2. In another embodiment, the method comprises an immunogenic amount of an MBP-MOMP polypeptide fusion protein.

The present invention further provides a method of preventing a *Chlamydia psittaci* infection in a subject comprising administering to the subject a vaccine comprising an immunizing amount of a nucleic acid vector for the transient expression in a eukaryotic cell comprising a eukaryotic promoter functionally linked to a nucleic acid encoding a *C. psittaci* MOMP polypeptide lacking regions VD1 and VD2 of MOMP. In a specific embodiment, the method comprises a nucleic acid encoding an amino acid sequence as set forth in SEQ ID NO:7 or SEQ ID NO:8.

In a specific embodiment, the present invention provides a method of preventing a *Chlamydia psittaci* infection in a subject comprising administering to the subject a vaccine comprising an immunizing amount of a nucleic acid vector for transient expression in a eukaryotic cell comprising a cytomegalovirus promoter functionally linked to a nucleic acid having the nucleotide sequence set forth in either SEQ ID NO:3, SEQ ID NO:4, SEQ ID NO:5 or SEQ ID NO:6.

Vaccine compositions can be administered to a subject or an animal model by any of many standard means for administering the particular composition. For example, compositions can be administered orally, sublingually, parenterally (e.g., intravenously), by intramuscular injection, by intraperitoneal injection, topically, transdermally, or the like. Compositions can be administered, for example as a complex with cationic liposomes, encapsulated in anionic liposomes, or encapsulated in microcapsules. Compositions can include various amounts of the selected composition in combination with a pharmaceutically acceptable carrier and, in addition, if desired, may include other medicinal agents, pharmaceutical agents, carriers, adjuvants, diluents, etc. Parental administration, if used, is generally characterized by injection. Injectables can be prepared in conventional forms, either as liquid solutions or suspensions, solid forms suitable for solution or suspension in liquid prior to injection, or as emulsions. Actual methods of preparing dosage forms are known, or will be apparent, to those skilled in this art; for example, see Martin, E. W., Ed., *Remington's Pharmaceutical Sciences*, latest edition, Mack Publishing Co., Easton, Pa.

In one embodiment, a vaccine of this invention, whether a protein or a nucleic acid vaccine, is administered on a regular booster schedule, for example, every six months, to companion birds of the order Psittaciformes. The vaccine may be advantageously administered to such birds orally, such as in pill form, or intranasally in a spray, or intraocularly in a drop. Alternatively, the vaccine may be administered intramuscularly or subcutaneously.

The following examples are intended to illustrate, but not limit, the invention. While they are typical of those that might be used, other procedures known to those skilled in the art may be alternatively employed.

EXAMPLES

Example 1

*C. psittaci* MOMP Genes

```
Using PCR primers 5GPF ACGCATGCAAGACACTCCTCAAAGCC;   (SEQ ID NO: 15) and
                  3GPB ACGAATTCCTAGGTTCTGATAGCGGGAC; (SEQ ID NO: 16),
```

a full-length *C. psittaci* MOMP gene was amplified, cloned and sequenced from a wild-type *C. psittaci* strain isolated from a cockatiel. The sequence of this cockatiel MOMP gene is identical to the MOMP gene sequences from *C. psittaci* strain MN and Avian Type C strain (Zhang et al. 1989). Previous work by Kaltenboeck et al. (1993) established that the MOMP gene sequence of *C. psittaci* strain B577 isolated from an aborted ovine fetus was identical to the MOMP gene sequence from a *C. psittaci* strain isolated from a parakeet.

Example 2

Vector Constructions

A. MOMP 3' Gene Fragment Cloning

```
Primer 3GPB      (ACGAATTCCTAGGTTCTGATAGCGGGAC; SEQ ID NO: 15)
and primer cBamA (CGGATCCATTACCCAAGGTGTTATGGA;  SEQ ID NO: 16)
```

were used for PCR amplification of DNA from the cockatiel *C. psittaci* strain ("LSUWTCK"). Primer cBamA was specifically designed to create a BamHI restriction site (GGATCC) for subsequent cloning purposes. For PCR amplification of MOMP DNA from strain B577, primer ParaBamG (TAAAGGATCCGCCATGGCAGC; SEQ ID NO: 18), which includes a BamHI site naturally present in the B577 sequence, was used in combination with primer 3GPB. The underlined bases in primer ParaBamG represent changes from the natural B577 sequence that create a start ATG codon and a Kozak consensus sequence.

The PCR-derived DNA fragments, which contain either the *C. psittaci* strain LSUWTCK MOMP gene fragment extending from nucleotide 540 to nucleotide 1266 (SEQ ID NO:3) or the *C. psittaci* strain B577 MOMP gene fragment extending from nucleotide 563 to 1249 (SEQ ID NO:5), were separately cloned into a plasmid vector pCR 2.1 (InVitrogen, Inc., Carlsbad, Calif. 92008), which contains a unique Bam-HI site. The orientation of the each cloned DNA fragment was such that after BamHI digestion an approximately 0.75 kb DNA fragment was produced and used as a source of MOMP DNA for the subsequent manipulations. The fragment from strain LSUWTCK encodes 222 amino acids from the MOMP gene and starts immediately after the second variable epitope (VD2) and includes all downstream regions (see Zhang et al. 1989). The fragment from strain B577 encodes 228 amino acids from the MOMP gene and also includes regions VD3 and VD4.

B. Fusion Protein Vector

A BamHI cockatiel MOMP gene fragment (SEQ ID NO: 3) in pCR 2.1, as described above, was cloned into the BamHI site in the bacterial expression vector pMAL™-c2 (New England Biolabs, Inc., Beverly, Mass. 01915-5999). This is a commercially available vector that is designed to create translation fusions between a cloned gene and the *E. coli* malE gene, which codes for maltose binding protein (MBP). The BamHI site in the bacterial expression vector pMAL™-c2 is in frame with the MBP gene. The BamHI site in the cBamA synthetic oligonucleotide primer was designed to be in the same reading frame with the MOMP gene. Consequently, the construct described herein will result in the expression of a MBP-MOMP fusion protein.

C. Mammalian Expression Vector

In addition to the engineered restriction enzyme site, primer cBamA has a base change from the native sequence, (G→A), creating a start codon (ATG) in frame with the MOMP coding sequence, so that the ribonucleic acid transcribed from the cloned sequence can be translated in eukaryotic cells. The particular location for the ATG was chosen due to the ability to create a Kozak box consensus sequence, $G(A)_{-3}$ $NNATGG(A)_{+4}$ around the start site, which enhances translatability in eukaryotes. Thus, the same BamHI cockatiel MOMP DNA fragment from plasmid pCR2.1 was also used for cloning into the plasmid pcDNA 3.1 $Zeo^+$ (InVitrogen, Carlsbad, Calif.), which is designed for high level stable and transient expression in mammalian hosts. This DNA, designated "pcDNA 3.1 $Zeo^+$/CpMOMP", was used for genetic immunization experiments after purification in CsCl gradients.

Example 3

Expression and Purification of MBP-MOMP Fusion Protein

A. Expression.

Protein production was carried out according to the instructions included in the manual from New England Biolabs, Inc.(Beverly, Mass. 01915-5599), except that cells were harvested after 3 hours of induction with Isopropyl-thio-galactoside (IPTG) with a final concentration of 0.3 mM. The pellet of the cells derived from 500 mL of media was resuspended in 25 mL of lysis buffer: 100 mM NaCl, 100 mM Tris HCl pH 8.0, 100 mM EDTA pH 8.0, and 10 mM EGTA pH 8.0. Fresh lysozyme 10 mg/mL (0.5 mL for 500 mL of media) was added and the sample was left on ice for 30 min at which time 1 mL of 25% Triton X100 (T100) was added and left on ice for 5 min. At this time the solution became viscous due to the released DNA.

B. Purification

The unexpected formation of inclusion bodies by the MBP-MOMP fusion protein in *E. coli* after IPTG induction, made it extremely easy to purify. The resultant solution after cell lysis was sonicated (5 times, 30 sec. each time or until the viscosity was eliminated) and subsequently 50 mL of lysis buffer was added. The sample was centrifuged at 5000 g, 20 min. at +4° C. The supernatant of the sample was discarded and the insoluble part containing the MBP-MOMP fusion protein in the form of inclusion bodies was recovered in the pelleted material. The pellet was washed 2 times with lysis buffer +0.5% T100 (49 mL of lysis buffer plus 1 mL of 25% T100) using a 10 min incubation time at room temperature.

The recovered material was resuspended in 25 mL of Lysis buffer without T100 and stored overnight on ice. The material was centrifuged at 5000 g, 20 min, +4° C., resuspended in 5 mL of Lysis buffer, added 45 mL of 6M urea, subsequently incubated for 15 min at room temperature, and finally centrifuged at 5000 g, 20 min at +4° C. The supernatant was recovered and diluted 1:4 with 5M urea and filtered through an AMICON DIAFLO® Ultrafilter, series XM (Amicon, Lexington, Mass. 02173), which had a molecular weight cutoff at 50,000, until the volume was approximately 10 mL. The total volume was adjusted with 5 M urea to 50 mL and the sample was dialyzed against Phosphate buffer saline (PBS) to decrease the urea concentration in the sample.

The first dialysis step was 2 hours against 100 mL of 2.5 M of urea, and the next 5 steps were against two-fold serially decreasing concentrations of 2.5 M urea. Four additional changes of dialysis buffer were performed using 5000 mL of PBS without urea. The final product was used for injections. The approximate yield of protein extracted from the cells grown in 1 Liter of media was 100 mg, resulting in a MOMP-MBP fusion protein purity of approximately 85%.

A pool of monoclonal antibodies raised against the *C. psittaci* strain 6BC and the *C. pecorum* MOMPs, which reacted with purified, native MOMP proteins from strains B577 and 6BC, also reacted with the MBP-MOMP fusion protein in western assays, demonstrating that the fusion protein retains epitopes found on the native protein. The reaction of the same antibodies with strain B577 and the MBP-MOMP fusion protein containing the MOMP polypeptide from strain LSUWTCK, shows that at least some antibodies can recognize MOMP proteins from different strains.

Example 4

Vaccination

A. Immunoblotting Assay

Cockatiel *C. psittaci* strain LSUWTCK, grown in Vero cells, was partially purified (Baghian, et al., 1990), resolved in SDS-PAGE and transferred onto nitrocellulose membranes (NCM). Strips cut from the blot were used to evaluate the antibody response to MOMP in vaccinated birds. A rabbit anti-cockatiel IgG produced in the inventors' laboratory was used to detect the cockatiel IgG responses to vaccines. Strips were blocked, reacted with cockatiel serum, then with the rabbit anti-cockatiel IgG followed by exposure to a hydrogen peroxidase conjugated goat anti-rabbit IgG and color-forming substrate.

B. Experimental Vaccination Design

1. Experiment B-1.

A total of 25 cockatiels were used. Five treatment regimes were designated, with five birds per treatment. Group I was the control group, which was not vaccinated. Groups II, III, and IV were vaccinated with the vaccines of this invention. In Group V, the birds were inoculated with inactivated elementary bodies from *C. psittaci*. The Groups were set up as follows:

| | |
|---|---|
| Group I: | No vaccine, control group |
| Group II: | pcDNA 3.1 $Zeo^+$/CpMOMP DNA vaccine |
| Group III: | MBP-MOMP fusion protein vaccine (Example 3A) |
| Group IV: | pcDNA 3.1 $Zeo^+$/CpMOMP DNA and MBP-MOMP fusion protein combination vaccine |
| Group V: | Vaccination with inactivated EBs |

2. Experiment B-2

A total of 21 cockatiels were used. Five treatment regimes were designated, with three birds in Group I, five birds each in Groups II and III, and four birds each in Groups IV and V. Group I was the control group, which was not vaccinated. Groups II and III were vaccinated with the vaccines of this invention. In Groups IV and V, the birds were inoculated with inactivated elementary bodies from *C. psittaci.*

The Groups Were Set Up as Follows:

| | |
|---|---|
| Group I: | No vaccine, control group |
| Group II: | pcDNA 3.1 Zeo$^+$/CpMOMP DNA vaccine |
| Group III: | MBP-MOMP fusion protein vaccine (Example 3A) |
| Group IV: | Vaccination with inactivated (by irradiation) EBs |
| Group V: | Vaccination with glutaraldehyde-treated, inactivated EBs |

C. Vaccination Protocol

1. Experiment B-1

Group I did not receive any vaccinations. For Group II 100 microliters of pcDNA 3.1 Zeo$^+$/CpMOMP DNA (1 microgram/microliter) mixed with 100 microliters of PBS. This mixture was injected in 4 sites using 50 microliters/site. For Group III vaccination, 1.7 milliliters (mL) of the MOMP-MBP fusion protein (1 microgram/microliter) was mixed with 1.7 mL Adju-Phos [Aluminum Phosphate Gel adjuvant (Superfos Biosector a/5, Inc., Denmark)], and 0.4 microliters were injected subcutaneously in each bird. For Group IV, each bird simultaneously received the same inoculations of Group II and Group III, therefore a combination "fusion-protein/DNA" vaccine. For Group V, the birds were injected with inactivated elementary bodies from *C. psittaci*, made according to the protocol described at C.3 below.

2. Experiment B-2.

Group I did not receive any vaccinations. For Group II 100 microliters of pcDNA 3.1 Zeo$^+$/CpMOMP DNA (1 microgram/microliter) mixed with 100 microliters of PBS. This mixture was injected as follows: 100 microliters were dropped into the nasal canals, 50 microliters into each side of the nose, and 100 microliters was injected at 3 sites in the chest muscle. For Group III vaccination, 1.7 milliliters (mL) of the MOMP-MBP fusion protein (1 microgram/microliter) was mixed with 1.7 mL Adju-Phos [Aluminum Phosphate Gel adjuvant (Superfos Biosector a/5, Inc., Denmark)], and 0.4 microliters were injected subcutaneously—injections were performed as described for Group II. For Groups IV and V, the birds were injected with inactivated elementary bodies from *C. psittaci,* inactivated either with cobalt source irradiation, or made according to the protocol in C.3. below, and then further treated by irradiation with a cobalt source.

3. Production of Inactivated EBs:

Four mL of a PBS solution containing *C. psittaci* strain LSUWTCK ($1.4\times10^8$/mL) were inactivated by treatment in 1 mL of PBS+0.5 mL glutaraldehyde (20%), at 4° C. overnight. EBs were pelleted and washed with 4 mL of PBS, resuspended in 4 mL of PBS, and tested for infectivity in cell culture. Residual infectivity was detected, so the EBs (3 ml) were treated again with 1 ml formaldehyde (final conc. 4%) for 6 hours at room temperature. EBs were again pelleted, washed once with PBS and resuspended in a PBS Adju-Phos (Sigma, Inc.). Each bird was inoculated with 0.5 ml of the final solution subcutaneously.

D. Vaccination Schedule

1. Experiment B-1.

On Oct. 1, 1996, the birds were bled for prevaccination serology tests. On the same day, first injections were given as follows:

| | |
|---|---|
| Group II: | intramuscularly |
| Group III: | subcutaneously |
| Group IV: | as in Group II and III |
| Group V: | subcutaneously |

On Nov. 4, 1996, the four groups were given second injections, identical to the ones indicated above. On Dec. 19, 1996, the four groups were given third injections, identical to the 1st and 2nd injections. On Jan. 14, 1997, the birds were bled again, then challenged with a 0.5 mL suspension of *C. psittaci* EBs containing at least $10^4$, preferably $5\times10^5$, infection forming units (IFU). These challenges were administered intranasally and by ocular drops, one in each eye.

2. Experiment B-2.

The schedule for this experiment generally paralleled the experiment above.

E. Results

1. Experiment B-1: Seroconversion

Bird sera taken after the third vaccine inoculation, just before the challenge with infectious EBs, were used in a immunoblotting assay. Among the four groups which were vaccinated, only Group III showed consistent seroconversion, in that two birds were strongly positive while three birds were weakly positive. One of the birds in Group V which was vaccinated with inactivated EBs also gave a strong reaction in the immunoblotting assay.

2. Experiment B-1: Protection from Challenge

The birds were evaluated for clinical signs over the months of January through March, 1997 following their challenge inoculation on January 14. The following observations were made:

Group I: This group of birds exhibited signs of bilateral conjunctivitis, irritated choana and stained vents (a sign of diarrhea). One bird in the group died 38 days post-exposure, and *C. psittaci* was cultured from this animal. Most birds in this group showed clinical improvement after 25 days post-exposure, until they were sacrificed.

Group II: The majority of this group showed mild, clinical signs associated with conjunctivitis, and an irritated choana (upper respiratory irritation). Little or no gastrointestinal abnormalities were noted. All birds survived and were sacrificed.

Group III: Three birds in this group showed very few clinical abnormalities during the trial, indicating that they were protected from the challenge. On days 3–5 after the challenge, bilateral conjunctivitis, irritated choanas and vent staining was apparent. Two of the birds died during the trial period.

Group IV: Four birds from this group exhibited minimal conjunctivitis through the trial period. One bird did show bilateral conjunctivitis with severe diarrhea, and it died early in the trial period.

Group V: The entire group of birds had bilateral conjunctivitis and choanal irritation through 75% of the vaccine trial period. This group of birds survived with minimal upper respiratory clinical abnormalities. No gastrointestinal abnormalities were noted. All birds were sacrificed at the end of the trial period.

3. Experiment B-2. Protection From Challenge

Group I birds showed moderate clinical signs of *Chlamydia psittaci* infection (see the description under Group I in Experiment B-1 above). Groups II and III were rated as being normal, i.e. all birds were clinically normal, except for a rare abnormality noted, such as conjunctivitis or nasal discharge, which were not considered to be treatment-related. Groups IV and V exhibited clinical signs and symptoms that were the same, or more severe than, the control Group I.

Example 5

Vaccination at Sites of Potential Invasion (Mucosal Immunity)

For a more complete immune response, vaccines may be delivered to the animals at the sites of potential invasion by *C. psittaci*, e.g. the oral or nasal mucosa. In a preferred embodiment, birds may be vaccinated by an intranasal route. Preparations of vaccine, as described in Example 4, can be administered to the nasal mucosa via a spray delivered intranasally to the bird, or through aerosolization of the vaccine. The latter may be effective when a large number of animals is to be vaccinated simultaneously. One of skill in the art will be familiar with the various techniques available and will be able to design a vaccination protocol appropriate for particular animal(s)' needs (see Tizard, Ian; "Veterinary Immunology: *An Introduction*", Fourth Edition, 1992, W.B. Saunders Company, Philadelphia, Pa., 498 pp.). Alternatively, the vaccines of this invention can also be administered through the feed or in the drinking water of the animal.

Although the present process has been described with reference to specific details of certain embodiments thereof, it is not intended that such details should be regarded as limitations upon the scope of the invention except as and to the extent that they are included in the accompanying claims.

REFERENCES

Baghian, A and K Schnorr. 1992. Detection and antigenicity of chlamydial proteins which bind eukaryotic cell membrane proteins.

Baghian, A, L Shaffer, and J Storz. 1990. Antibody response to epitopes of chlamydial major outer membrane proteins on infectious elementary bodies and of the reduced polyacrylamide gel electrophoresis-separated form. Infect. Immun. 58:1379–1383.

Hodinka, R L, CH Davis, J Choong, P B Wyrick. 1988. Ultrastructural study of endocytosis of Chlamydia trachomatis by McCoy cells. Infect. Immun. 56: 1456–1463.

Kaltenboeck, B, K G Kousoulas, J Storz. 1993. Structures of and allelic diversity and relationships among the Major Outer Membrane Protein (ompA) Genes of the four chlamydial species. J. Bacteriol. 175: 487–502.

Manning, D S and J S Stewart. 1993. Expression of the major outer membrane protein of *Chlamydia trachomatis* in *Escherichi coli*. Infect. Immun. 61: 4093–4098.

Peeling, R, I W McClean, R C Brunham. 1984. In vitro neutralization of *Chlamydia trachomatis* with monoclonal antibodies to an epitope on the major outer membrane protein. Infect. Immunol. 46:484–488.

Perez-Martinez, J A and J Storz. 1985. Antigenic diversity of *Chlamydia psittaci* of mammalian origin determined by microimmunofluorescences. Infect. Immun. 50: 905–910.

Pickett, M A, M E Ward, I N Clarke. 1988. *Chlamydia psittaci* ewe abortion agent: complete nucleotide sequence of the major outer membrane protein gene. FEMS Microbiol. Lett. 55: 229–234.

Spears, P and J Storz. 1979. Biotyping of *Chlamydia psittaci* based on inclusion morphology and response to diethylamino-ethyl-dextran and cycloheximide. Infect. Immun. 24: 224–232.

Storz, J. 1988. Overview of animal diseases induced by chlamydial infections, p. 167–192 In A L Barron (ed.), Microbiology of chlamydia. CRC Press, Inc., Boca Raton, Fla. Su, H and H D Caldwell. 1991. In vitro neutralization of *Chlamydia trachomatis* by monovalent Fab antibody specific to the major outer membrane protein. Infect. Immun. 59: 2843–2845.

Yuan, Y, Y X Zhang, N G Watkins, H D Caldwell. 1989. Nucleotide and deduced amino acid sequences for the four variable domains of the major outer membrane proteins of the *Chlamydia trachomatis* serovars. Infect. Immun. 57:1040–1049.

Zhang, Y X, S G Morrison, H D Caldwell, W Baehr. 1989. Cloning and sequence analysis of the major outer membrane protein genes of two *Chlamydia psittaci* strains. Infect. Immun. 57: 1621–1625.

What is claimed is:

1. A method of preventing a *Chlamydia psittaci* infection in an avian subject comprising administering to the subject an immunizing amount of an nucleic acid plasmid expression vector comprising a eukaryotic promoter functionally linked to a nucleic acid encoding a *C. psittaci* major outer membrane protein (MOMP) polypeptide lacking regions VD1 and VD2.

2. The method of claim 1, wherein the nucleic acid encodes a polypeptide with an amino acid sequence selected from the group consisting of: SEQ ID NO: 7 and SEQ ID NO:8.

3. The method of claim 1, wherein the eukaryotic promoter is the cytomegalovirus promoter.

* * * * *